United States Patent [19]
Haikala et al.

[11] Patent Number: 5,968,959
[45] Date of Patent: Oct. 19, 1999

[54] METHOD FOR THE PREVENTION AND TREATMENT OF STUNNED MYOCARDIUM

[75] Inventors: Heimo Haikala, Espoo; Petri Kaheinen, Helsinki; Jouko Levijoki, Espoo; Juha Kaivola, Helsinki; Martti Ovaska; Jarmo Pystynen, both of Espoo, all of Finland

[73] Assignee: Orion Corporation, Espoo, Finland

[21] Appl. No.: 09/188,707

[22] Filed: Nov. 10, 1998

Related U.S. Application Data

[63] Continuation-in-part of application No. 08/990,146, Dec. 12, 1997, abandoned.

[51] Int. Cl.$^6$ .......................... A61K 31/44; A61K 31/41; A61K 31/35
[52] U.S. Cl. ..................... 514/345; 514/382; 514/456
[58] Field of Search ..................... 514/345, 382, 514/456

[56] References Cited

U.S. PATENT DOCUMENTS

| | | | |
|---|---|---|---|
| 3,259,635 | 7/1966 | Ritter et al. | 260/343.2 |
| 3,515,721 | 6/1970 | Ritter et al. | 260/247.2 |
| 4,349,566 | 9/1982 | della Valle | 424/281 |
| 4,452,811 | 6/1984 | della Valle | 424/281 |

OTHER PUBLICATIONS

Ferrari, B., et al., "Development of Tetrazole Bioisosteres in Angiotensin II Antagonists," *Bioorg. & Med. Chem. Lett.* 4(1):45–50 (1994).

Gao, Y., et al., "Interaction of calmodulin with phospholamban and caldesmon: comparative studies by $^1$H–NMR spectroscopy," *Biochim. Biophys. Acta* 1160:22–34 (1992).

Hoh, J.F.Y., "Muscle fiber types and function," *Curr. Opin. Rheum.* 4:801–808 (1992).

Kohara, Y., et al., "Synthesis and Angiotensin II Receptor Antagonistic Activities of Benzimidazole Derivatives Bearing Acidic Heterocycles as Novel Tetrazole Bioisosteres," *J. Med. Chem.* 39:5228–5235 (Dec. 1996).

Lalli, J., et al., "Targeted Ablation of the Phospholamban Gene Is Associated With a Marked Decrease in Sensitivity in Aortic Smooth Muscle, " *Circ. Res.* 80(4):506–513 (Apr. 1997).

Lindemann, J.P., et al., "β–Adrenergic Stimulation of Phospholamban Phosphorylation and $Ca^{2+}$—ATPase Activity in Guinea Pig Ventricles," *J. Biol. Chem.* 258(1):464–471 (1983).

Marban, E., "Myocardial Stunning and Hibernation: The Physiology Behind the Colloquialisms," *Circulation* 83(2):681–688 (1991).

O'Neil, K.T., and DeGrado, W.F., "How calmodulin binds its targets: sequence independent recognition of amphiphilic α–helices," *Trends Biochem. Sci.* 15:59–64 (1990).

STN Database CAPLUS, Document No. 77:88302, Murakami, M., et al., "Bis(carboxymethoxy)–4–methylcoumarins," (1972).

STN Database CAPLUS, Document No. 114:42491, Verma, B.S., et al., "Studies of pesticides based on coumarin: Part 5. Synthesis and antifungal activity of substituted 2,3–dihydrocyclopenta[c][1] benzopyran–4(H)–ones," (1989).

STN Database CAPLUS, Document No. 97:216033, Winter, W., et al., "Tricyclic aryl ethers and medicines containing these compounds," (1982).

STN Database CAPLUS, Document No. 97:216005, Lesher, G.Y., and Philion, R.E., "3–Substituted–6–(lower alkyl)–5–(pyridinyl)–2(1H)–pyridinones, their cardiotonic use and intermediates therefor," (1982).

STN Database CAPLUS, Document No. 84:179971, Bartl, K., et al., "Synthesis of .DELTA.8–tetrahydrodibenzo[b,d] pyran–6–ones and their aminolysis to .DELTA.8–tetrahydrophenanthridine–6–ones," (1976).

STN Database CAPLUS, Document No. 84:179968, Chebaane, K., et al., "Synthesis of 2–arylnaphthalenes and of dibenzocoumarins. I. Synthesis of tetrahydrodibenzocoumarins, 2–(1–cyclohexenyl)naphthalenes and tetrahydrobenzocoumarins," (1975).

*Primary Examiner*—Raymond Henley, III
*Attorney, Agent, or Firm*—Sterne, Kessler, Goldstein & Fox PLLC

[57] ABSTRACT

A method for the prevention and treatment of stunning of the heart subsequent to ischemia-reperfusion is described. The method comprises administering a therapeutically effective amount of a phospholamban inhibitor to a patient. Phospholamban inhibitors relieve the inhibitory effect of phospholamban on cardiac sarcoplasmic reticulum $Ca^{2+}$-ATPase.

23 Claims, 4 Drawing Sheets

METHOD FOR THE PREVENTION AND TREATMENT OF STUNNED MYOCARDIUM

CROSS-REFERENCE TO RELATED APPLICATIONS

This application is a continuation-in-part (CIP) of U.S. application Ser. No. 08/990,146, filed Dec. 12, 1997, now abandoned, which is herein incorporated by reference.

BACKGROUND OF THE INVENTION

This invention relates to a method for the prevention and treatment of stunned heart phenomenon. Particularly, the invention relates to a method for the prevention and treatment of stunning of the myocardium in association with ischemia-reperfusion. The cardiovascular interventions and conditions accompanied with the ischemia-reperfusion and subsequent stunning include e.g. thrombolysis of myocardial infarction, coronary balloon angioplasty and coronary stent implantation, coronary artery bypass surgery and other open-heart operations, coronary atherectomy, unstable angina, heart transplantation, resuscitation and valvular heart disease. The method for the prevention or treatment of stunned myocardium comprises administering a phospholamban inhibitor as the active compound.

The contraction of cardiac muscle cell is caused by calcium ions released from the intracellular calcium stores of the sarcoplasmic reticulum (SR). After triggering a cascade of events leading to cell shortening and muscle contraction a major part of calcium is reuptaken to the SR by the enzyme called $Ca^{2+}$ATPase and a minor part of calcium is extruded out of the cell. The $Ca^{2+}$ATPase is functioning under the inhibitory control of a small protein called phospholamban. The unphosphorylated form of phospholamban inhibits the $Ca^{2+}$ATPase. The phosphorylation of phospholamban relieves this inhibition which is then seen as a stimulation of the $Ca^{2+}$ATPase. The relief of the phospholamban inhibition on the $Ca^{2+}$ATPase stimulates the uptake of calcium from the cytoplasm into the SR which then finally increases the amount of calcium for the next contraction. In addition to the phosphorylation based regulation the inhibition of the $Ca^{2+}$ATPase by phospholamban can be eliminated also by compounds which directly bind to phospholamban. Such compounds (phospholamban inhibitors) eliminate the inhibitory action of phospholamban on the SR $Ca^{2+}$-ATPase like the protein kinases as they phosphorylate phospholamban.

One of the pathological phenomena in the function of the heart is called stunned myocardium in which the contraction force is decreased despite the normal coronary flow. The stunning is developed as a consequence of the ischemic period (=marked decrease in the coronary flow) followed by reperfusion of the myocardium. It is typical that in the stunned myocardium the decreased contraction force is not accompanied with the decrease in the amount of calcium released from the SR. On the contrary, there is higher amount of calcium in the SR available for contraction trigger in stunned myocardium (Marban, E., "Myocardial stunning and hibernation. The physiology behind the colloquialisms", Circulation, 83(2):681–688, 1991). Therefore, the stimulation of the calcium uptake into the SR is not expected to change the stunning in the myocardium.

SUMMARY OF THE INVENTION

It has now been found that compounds which are effective in relieving the inhibitory effects of phospholamban on cardiac SR $Ca^{2+}$-ATPase through direct binding to the phospholamban protein (phospholamban inhibitors) are effective in the prevention and treatment of stunned myocardium. Since the pathophysiology of the stunned myocardium is not related to the lack of calcium in the SR, it was unexpected that the elimination of the phospholamban inhibition on the $Ca^{2+}$ATPase abolished the development of post-ischemic stunning of myocardium.

DETAILED DESCRIPTION OF THE INVENTION

Figure 1:
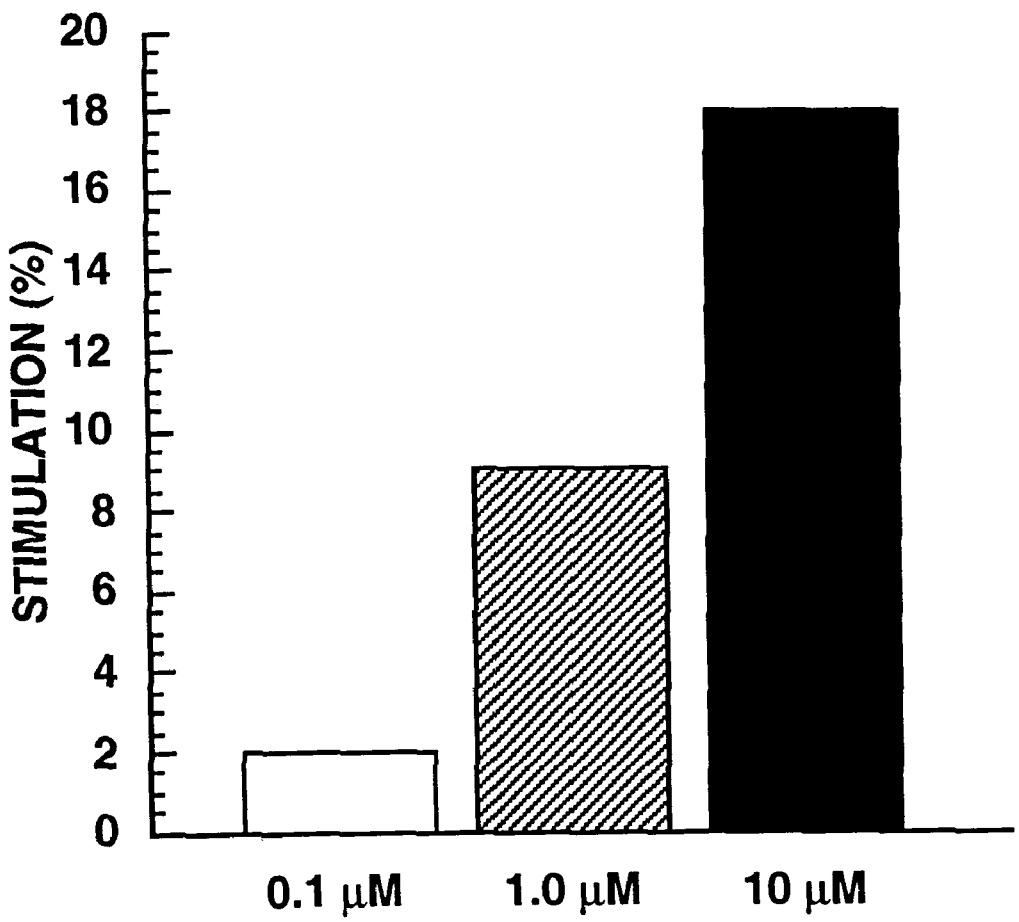
FIG. 1 shows the effect of compound of Example 8g (0.1, 1.0 and 10 $\mu$M) on the $Ca^{2+}$ uptake into the cardiac muscle SR vesicles.

The present invention provides a method for the prevention and treatment of stunned myocardium which comprises administering a therapeutically effective amount of a phospholamban inhibitor as the active compound to a mammal in need of such treatment or prevention. Particularly, the invention relates to a method for the prevention and treatment of stunning of the myocardium in association with ischemia-reperfusion. Thus the invention provides a method for the prevention and treatment of stunned myocardium in association with cardiovascular interventions and pathological conditions accompanied with the ischemia-reperfusion such as e.g. thrombolysis of myocardial infarction, coronary balloon angioplasty and coronary stent implantation, coronary artery bypass surgery and other open-heart operations, coronary atherectomy, unstable angina, heart transplantation, resuscitation and valvular heart disease.

The term "phospholamban inhibitor" means here a compound which relieves the inhibitory effect of phospholamban on SR $Ca^{2+}$-ATPase by direct binding to the phospholamban protein.

The inhibitory effect of a given compound on phospholamban can be demonstrated by measuring the effect of the compound on calcium uptake into the SR vesicles prepared from cardiac tissue and into SR vesicles prepared from fast skeletal muscle (psoas m.). Both kind of SR vesicles contain $Ca^{2+}$-ATPase but the vesicles from the fast skeletal muscle do not contain phospholamban (Hoh JFY, "Muscle fiber types and function", Current Opinion in Rheumatology, 4:801–808, 1992). An increase in the calcium uptake into the SR vesicles prepared from cardiac tissue but not into the SR vesicles prepared from fast skeletal muscle indicates that the compound relieves the inhibitory effect of phospholamban on SR $Ca^{2+}$-ATPase by direct binding to the phospholamban protein and that the compound is applicable as a phospholamban inhibitor in the method of the invention. The direct binding of a compound to the phospholamban protein can be ascertained by the circular dichroism (CD) spectroscopy. The methods for determining whether a compound relieves the inhibitory effect of phospholamban on SR $Ca^{2+}$-ATPase by direct binding to the phospholamban protein, i.e. is a phospholamban inhibitor, are illustrated in detail in the experimental section.

Phospholamban inhibitors suitable for use in the method of the invention include, but are not limited to, compounds of formula (I) or (II):

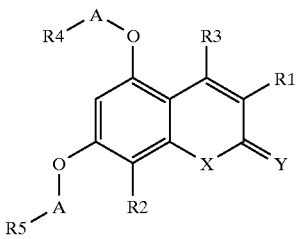
(I)

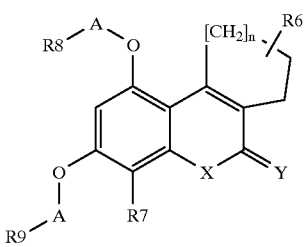
(II)

in which $R_1$ is hydrogen, alkyl, alkenyl, aryl, arylalkyl, hydroxyalkyl, halogenalkyl, alkoxy, $COR_{10}$, $CONR_{10}R_{11}$, $OR_{10}$, $S(O)_mR_{10}$, $NR_{10}COR_{11}$ or $NR_{10}R_{11}$, where $R_{10}$ is hydrogen, alkyl, alkenyl, aryl, arylalkyl, hydroxyalkyl, halogenalkyl, alkoxy or hydroxy and $R_{11}$ is hydrogen, alkyl, aryl, arylalkyl, alkoxy, aryloxy, hydroxy or acyl, or in case where X is $NR_{11}$, can $R_1$ also be carboxylalkyl, $R_6$ is hydrogen, alkyl, alkenyl, aryl, arylalkyl, $R_2$ and $R_7$ mean hydrogen, alkyl, aryl, arylalkyl, alkenyl, $COR_{10}$, $CONR_{10}R_{11}$, halogen, trifluoromethyl, nitro or cyano, where $R_{10}$ and $R_{11}$ are defined as above, $R_3$ is hydrogen, alkyl, aryl or arylalkyl, A means alkyl or substituted alkyl, m is 0–2 and n is 1–3, Y means O, NR11 or S, where R11 is the same as above, X means O, NR11 or S, where R11 is the same as above, $R_4$, $R_5$, $R_8$ and $R_9$ mean independently one of the following groups:

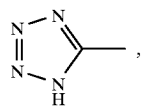

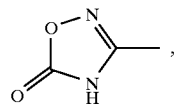

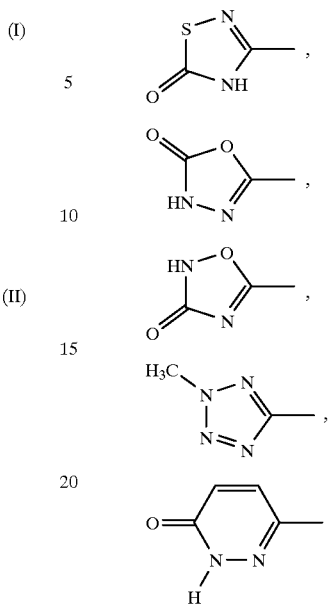

or in case where X is $NR_{11}$, can $R_4$, $R_5$, $R_8$ and $R_9$ also independently mean HOOC—, $R_{12}$OOC—, $H_2$NCO— or HOHNCO— wherein $R_{12}$ means alkyl, arylalkyl or aryl, and wherein each aryl residue defined above by itself or as part of another group may be substituted, and pharmaceutically acceptable salts and esters thereof.

The compounds of formula (I) or (II) can be prepared from the 1,3-dihydroxy substituted heteroaromatics by alkylation of the dihydroxy compounds by suitable alkylating agents, for example by chloroacetonitrile or bromoacetic ester according to the following Scheme 1, wherein $R_1$, $R_2$, $R_3$, X and Y are the same as defined above, R' is a protecting group for the hydroxyl, e.g. methyl, benzyl or tetrahydropyranyl.

SCHEME 1
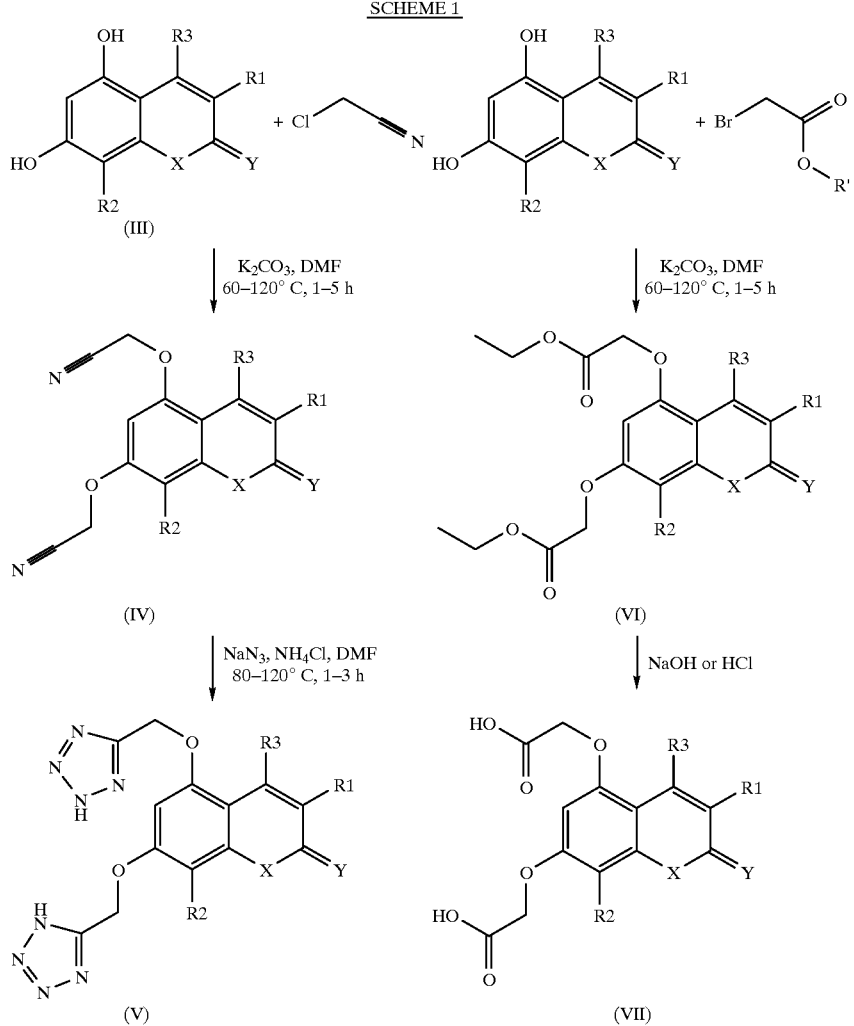
The cyano compound (IV) described above is used to prepare the 1,2,4-oxadiazole and 1,2,4-thiadiazole derivatives using the methods described in J. Med. Chem. 1996, 39, 5228–5235.
The syntheses are shown in Scheme 2, wherein $R_1$, $R_2$, $R_3$, X and Y are the same as defined above.
SCHEME 2
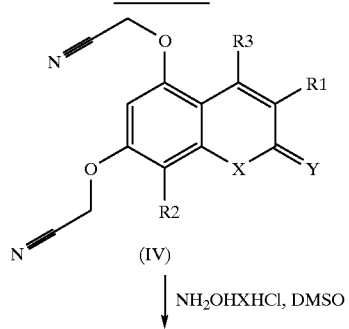

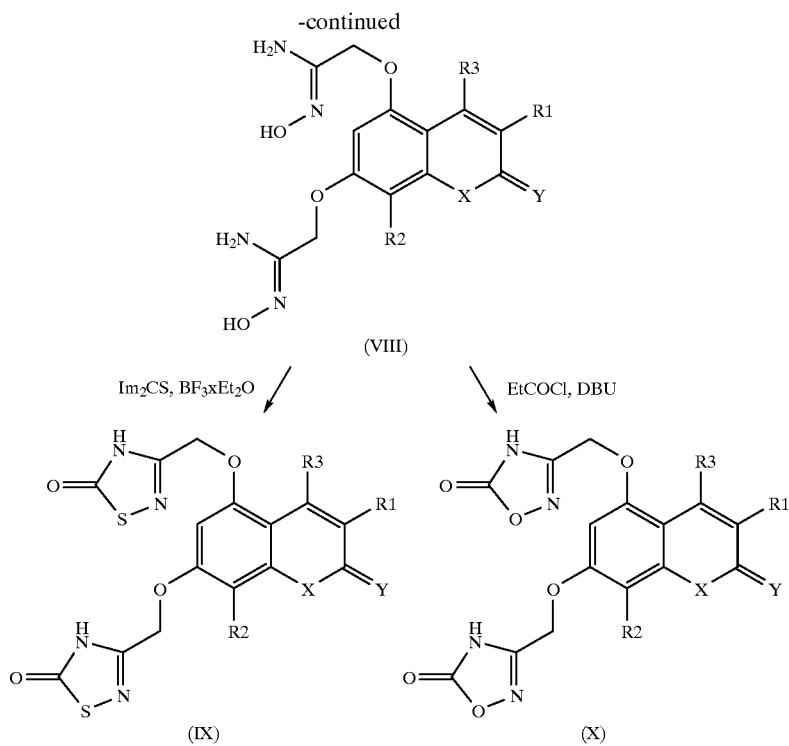

The other heterocyclics as groups $R_4$, $R_5$, $R_8$ and $R_9$ are prepared as described in Bioorg. Med. Chem. Lett., 1994, 4, 45–50.

The dihydroxyaromatics (III) are made by use of the literature methods. The coumarins (XIV), (XVI) and (XX) are made by the use of the Knoevenagel condensation or von Pechmann reaction as presented in Scheme 3 and 4, where $R_1$, $R_2$ and $R_3$, are the same as defined above, Z is alkyl, aryl, arylalkyl or alkenyl and R' is a protecting group for the hydroxyls e.g. methyl, benzyl or tetrahydropyranyl.

SCHEME 3

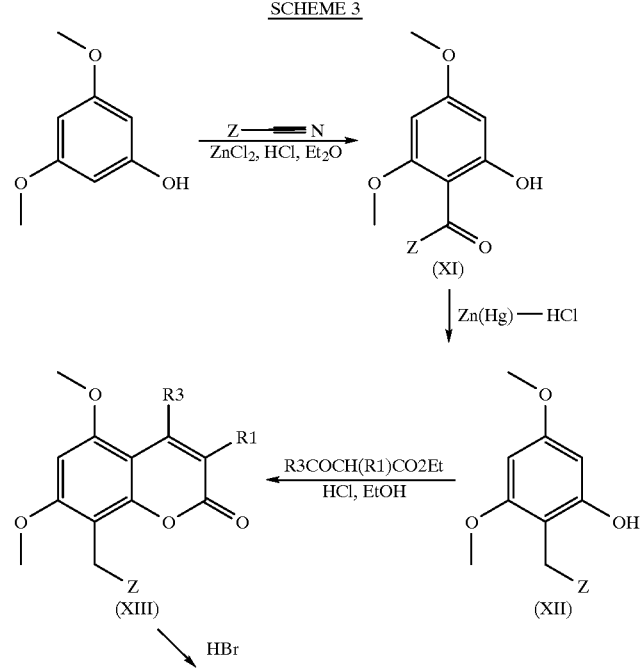

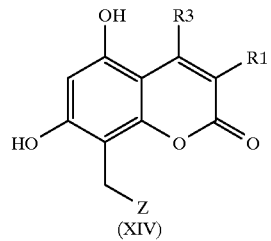
(XIV)
SCHEME 4
A
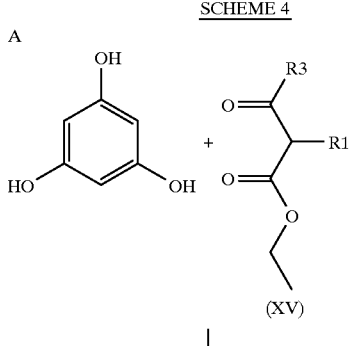
B
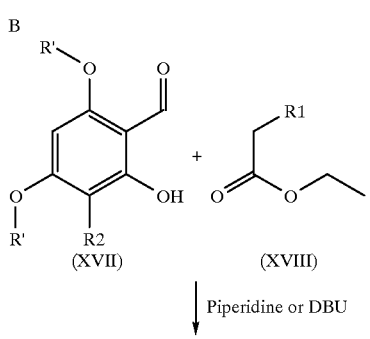
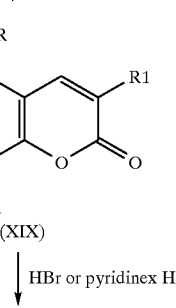
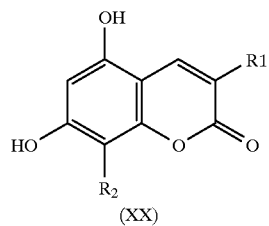
(XX)
The quinolinones are prepared by the Knorr reaction as described in Scheme 5, wherein $R_1$, $R_{11}$ and $R_3$ are the same as defined above, X is a halogen.
SCHEME 5
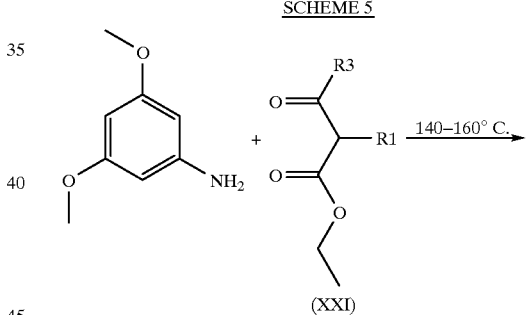
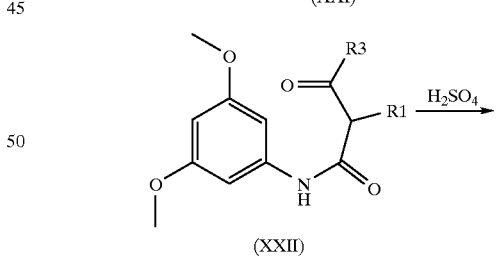
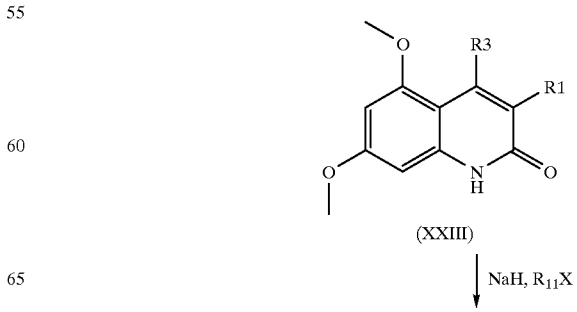

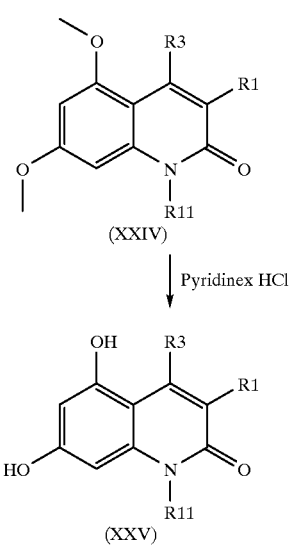

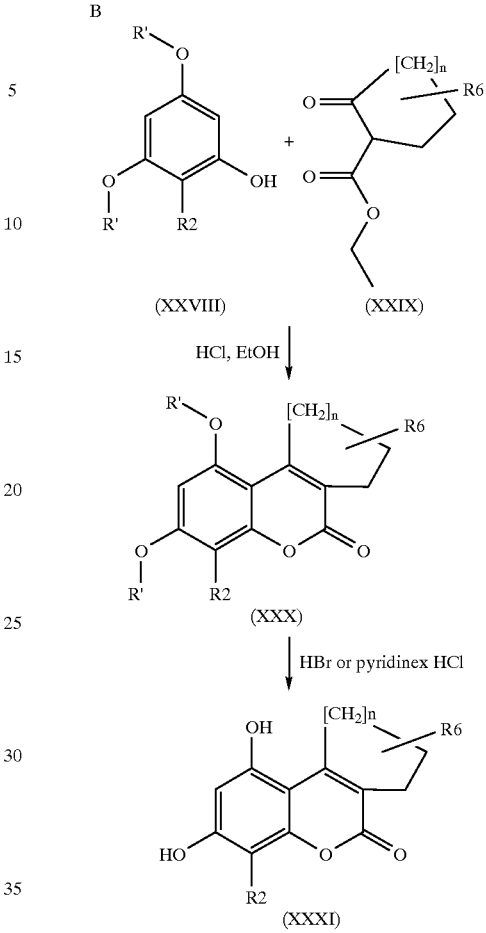

The cyclic compounds (11) can be prepared correspondingly from compound (XXXI) which can be prepared according to the Scheme 6, wherein $R_2$ and $R_6$ are the same as defined above, R' is a protecting group for the hydroxyls e.g. methyl, benzyl or tetrahydropyranyl.

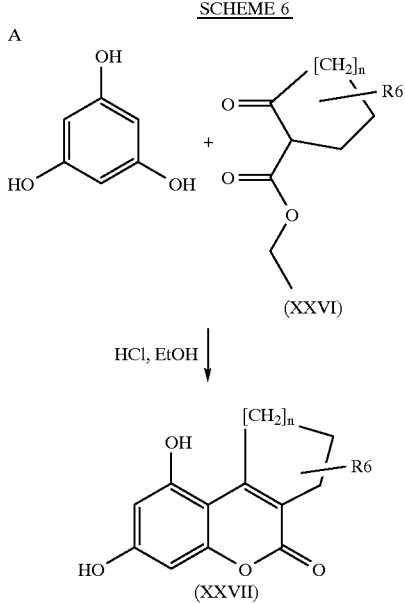

Cyclic quinolinone compounds (II) can be prepared correspondingly from (XXVI) using Scheme 5.

Salts and esters of the compounds, when applicable, may be prepared by known methods. Physiologically acceptable salts are useful as active medicaments, however, preferred are the salts with alkali or alkaline earth metals. Physiologically acceptable esters are also useful as active medicaments. Examples are the esters with aliphatic or aromatic alcohols.

The term "alkyl" as employed herein by itself or as part of another group includes both straight and branched chain radicals of up to 18 carbon atoms, preferably 1 to 8 carbon atoms, most preferably 1 to 4 carbon atoms. The term "lower alkyl" as employed herein by itself or as part of another group includes both straight and branched chain radicals of 1 to 7, preferably 1 to 4, most preferably 1 or 2 carbon atoms. Specific examples for the alkyl and lower alkyl residues, respectively, are methyl, ethyl, propyl, isopropyl, butyl, tert. butyl, pentyl, hexyl, octyl, decyl and dodecyl including the various branched chain isomers thereof.

The term "acyl" as employed herein by itself or as part of another group refers to an alkylcarbonyl or alkenylcarbonyl group, the alkyl and alkenyl groups being defined above.

The term "aryl" as used herein by itself or as part of another group refers to a monocyclic or bicyclic group containing from 6 to 10 carbon atoms in the ring portion. Specific examples for aryl groups are phenyl, naphtyl and the like. "Aroyl" means in a corresponding way an arylcarbonyl group.

The term "alkoxy" as employed herein by itself or as part of another group includes an alkyl group as defined above linked to an oxygen atom. "Aryloxy" means in a corresponding way an aryl group linked to an oxygen atom.

The term "substituted" as used herein in connection with various residues refers to halogen substituents, such as fluorine, chlorine, bromine, iodine or trifluoromethyl group, amino, alkyl, alkoxy, aryl, alkyl-aryl, halogen-aryl, cycloalkyl, alkylcycloalkyl, hydroxy, alkylamino, alkanoylamino, arylcarbonylamino, nitro, cyano, thiol, or alkylthio substituents.

The "substituted" groups may contain 1 to 3, preferably 1 or 2, most preferably 1 of the above mentioned substituents.

Phospholamban inhibitors such as compounds of formula (I) or (II) may be administered to a patient in therapeutically effective amounts which range usually from about 0.1 to 500 mg, more usually from about 0.5 to 50 mg, per day depending on the age, weight, condition of the patient, administration route and the phospholamban inhibitor used. The term "therapeutically effective amount" means here an amount which produces a inhibitory or preventive effect on the stunned myocardium phenomenon in a patient. The active compound of the invention, which can be compound of formula (I) or (II) or any compound possessing phospholamban inhibiting activity as defined above, can be formulated into dosage forms using the principles known in the art. It can be given to a patient as such or in combination with suitable pharmaceutical excipients in the form of tablets, dragees, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

EXPERIMENTS

Experiment 1

Effect of Phospholamban Inhibitors on Calcium Uptake into the SR Vesicles Prepared From Cardiac and Fast Skeletal Muscle The inhibitory effect of a given compound on phospholamban can be demonstrated by measuring the effect of the compound on calcium uptake into the SR vesicles prepared from cardiac tissue and into SR vesicles prepared from fast skeletal muscle (psoas m.). Both kind of SR vesicles contain $Ca^{2+}$-ATPase but the vesicles from the fast skeletal muscle do not contain phospholamban (Hoh JFY, "Muscle fiber types and function", Current Opinion in Rheumatology, 4:801–808, 1992). An increase in the calcium uptake into the SR vesicles prepared from cardiac tissue but not into the SR vesicles prepared from fast skeletal muscle indicates that the compound relieves the inhibitory effect of phospholamban on SR $Ca^{2+}$-ATPase and thus acts as a phospholamban inhibitor.

Preparation of the SR-vesicles

Guinea pigs (10–12) were decapited. Their hearts or the psoas muscles were excised, washed in ice-cold 0.9% NaCl and cut into pieces in a buffer containing 20 mM Tris-maleate, 0.3 M sucrose, pH 7.0. Thereafter tissue pieces were homogenized with Polytron and further with Potter (10 strokes). The homogenate was centrifugated at 1000 g for 15 min at 4° C. The supernatant was collected and the pellet was resuspended into 5 ml of the buffer (20 mM Tris-maleate, 0.3 M sucrose, pH 7.0) and recentrifugated at 1000 g for 10 min at 4° C. The obtained supernatant was combined with the earlier collected supernatant and centrifugated once again at 10 000 g for 20 min at 4° C. The final supernatant was filtered into a bottle equipped with a magnetic stirrer. KCl was added to the filtered supernatant to achieve the final concentration of 0.6 M (at 4° C.). The obtained solution was centrifugated at 100 000 g for 60 min at 4° C. The pellet was suspended in 5 ml of the buffer containing 20 mM Tris-maleate, 0.3 M sucrose, pH 7.0 and centrifugated at 100 000 g for 60 min at 4° C. The obtained pellet was suspended in 5 ml of buffer containing 20 mM Tris-maleate, 0.3 M sucrose, 0.1 M KCl, pH 7.0 and stored at −80° C. until use. The protein concentration was also measured in order to standardise the separately prepared vesicle preparations.

Calcium Uptake Assay

In the calcium uptake assay, the fluorescent indicator, fluo-3 was used to detect the decrease of the extravesicular $Ca^{2+}$-concentration, when the SR $Ca^{2+}$ATPase was transferring $Ca^{2+}$ from the extravesicular space into the SR-vesicles.

The SR-vesicles obtained above (50 µg protein/ml) were pre-incubated with or without the test compound at 37° C. for 5 min in the assay buffer containing 40 mM imidazole, 95 mM KCl, 5 mM $NaN_3$, 5 mM $MgCl_2$, 0.5 mM EGTA, 5 mM potassium oxalate, 2 µM ruthenium red, 5 µM fluo-3, pH 7.0. The free calcium was adjusted to 0.1 µM or to 0.04 µM by $CaCl_2$. The reaction was initiated by adding ATP (5 mM). The final reaction volume was 1.5 ml. The fluorescence of reaction mixture was measured for 3 min by using the excitation and emission wavelengths of 510 nm and 530 nm, respectively.

Results

FIG. 1 shows the effect of a phospholamban inhibitor of Example 8g (0.1, 1.0 and 10 µM) on the $Ca^{2+}$ uptake rate into the cardiac muscle SR vesicles. It can be seen that compound of Example 8g accelerated the calcium uptake into the cardiac SR vesicles. In contrast, compound of Example 8g did not change the calcium uptake into the SR vesicle prepared from the fast skeletal muscle at 0.1–10 µM concentrations.

Table 1 shows the effects of various other phospholamban inhibitors of formula (I) or (II) on the $Ca^{2+}$ uptake rate into the cardiac (A) and fast skeletal muscle (B) SR vesicles. The experiments were carried out at 0.1 µM and 0.04 µM free calcium concentrations, respectively.

TABLE 1

Stimulation (%) of the $Ca^{2+}$ uptake into the vesicle preparations obtained from the ventricular myocardium (A) and fast skeletal muscle (B) of the guinea-pig heart.

| Compound of Example No. (100 μM) | The stimulation (%) of $Ca^{2+}$ uptake | |
|---|---|---|
| | A | B |
| 1c | 42 | −6 |
| 2c | 26 | −1 |
| 3c** | 51 | 0 |
| 7c | 5 | −17 |
| 8g* | 18 | 0 |
| 11b | 28 | nd |
| 12 | 32 | nd |
| 13d*** | 23 | nd |
| 14c* | 18 | nd |
| 18e | 13 | nd |
| 21 | 11 | nd |
| 23**** | 20 | nd |

*10 μM, 20 μM, *50 μM, ****5 μM
nd = not determined

Experiment 2

Binding of a Phospholamban Inhibitor of Example 1c to the Cytosolic Part of Phospholamban Demonstrated by the Circular Dichroism (CD) Spectroscopy Both the 36 amino acid N-terminal fragment of human phospholamban (PLB [1–36 a.a.]) and the 36 amino acid N-terminal fragment of double phosphorylated human phospholamban (PLB [1–36 a.a.](Ser16PO$_3$-, Thr17PO$_3$-)) were obtained by peptide synthesis. The peptides were purified by reverse phase HPLC, analysed for homogenity by mass spectrometry and were found pure at 97%. The peptides were lyophilized and then resuspended in water at the final concentration of 0.1 mM, for CD analysis. The pH of both solutions was between 3 and 4 and was not further adjusted. Compound of Example 1c was solved in water at a final concentration of 0.1 mM. The pH was adjusted at 7.2 by adding 1 N NaOH.

Circular dichroism spectra were acquired at 24° C. on samples of 100 μl. The spectra were recorded on a Jasco J-720 spectropolarimeter using a 1 mm path-length quartz cuvette. The band width was 1 nm, the sensitivity 20 mdeg, the step resolution 0.5 nm, the response time 0.5 sec, and the scan speed 20 nm/min (from 250 to 190 nm). The spectra were expressed in $[\theta] \times 10^{-3} \times degrees \times cm^2 \times dmol^{-1}$.

Figure 2:
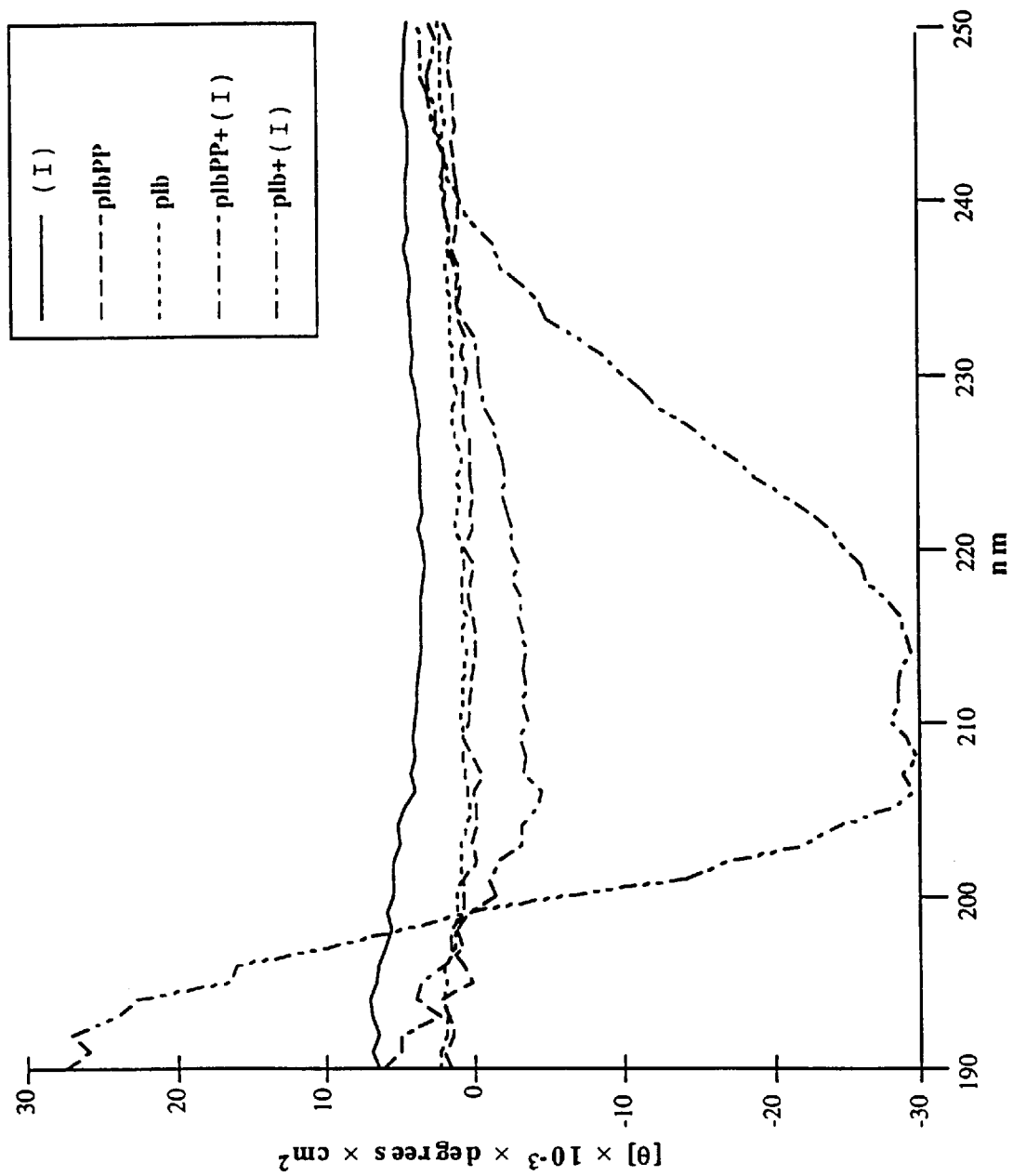
FIG. 2 shows CD spectra of 50 $\mu$M of PLB[1–36 a.a] (plb), PLB[1–36 a.a.](Ser16PO$_3$-, Thr17PO$_3$-) (plbPP), compound of Example 1c, and of the mixtures PLB[1–36 a.a]+compound of Example 1c and PLB[1–36 a.a.] (Ser16PO$_3$-, Thr17PO$_3$-)+compound of Example 1 c in water at room temperature.

The CD spectra of PLB[1–36 a.a] and of the mixtures PLB[1–36 a.a]+compound of Example 1c show that a dramatic change in the average structure of the peptide takes place after addition of compound of Example 1c. A marked increase of α-helical contribution can be seen (FIG. 2). Such a behaviour was shown for many Calmodulin-binding peptides, which form helices in the bound state. CD studies showed that when such peptides bind Calmodulin, there is an increase in helicity of the complex over the sum of the two individual non interacting components (for a review, see: O'Neil, K. T. and DeGrado, W. F. "How calmodulin binds its targets: sequence independent recognition of amphiphilic α-helices", TIBS 15:59–64, 1990). Moreover, it was previously demonstrated by NMR that the N-terminal fragment of PLB [aa.1–25] interacts directly with Calmodulin (Gao, Y. et al. "Interaction of calmodulin with phospholamban and caldesmon: comparative studies by $^1$H-NMR spectroscopy", Biochim. Biophys. Acta 1160: 22–34, 1992).

The present experiment thus verifies that compound of Example 1c forms a complex with PLB at his N-terminal domain.

Compound of Example 1c, added to PLB[1–36 a.a.] (Ser16PO$_3$-, Thr17PO$_3$-), is not influencing the structure of the phosphorylated peptide as much as for the phosphorylated. The CD measurements show that compound of Example 1c interacts with the cytosolic part of phospholamban PLB[1–36 a.a.], and does not interact or interacts weakly with the phosphorylated phospholamban (PLB[1–36 a.a.](Ser16PO$_3$-, Thr17PO$_3$-)). Thus, the interaction is specific for the unphosphorylated phospholamban.

Experiment 3

Effect on the Development of Stunned Myocardium in Isolated Guinea-pig Langendorff Heart Method Guinea-pigs of either sex weighing 300–400 g were used in the study. After the guinea-pig was sacrificed by a blow on the skull and decapitated the heart was rapidly excised. The heart was then rinsed in oxygenated perfusion buffer. A cannula was inserted into the aorta and secured with a ligature. Retrograde perfusion began as soon as the heart was placed in a thermostatically controlled moist chamber of the Langendorff apparatus. Modified Tyrode solution (37° C.), equilibrated in a thermostatically controlled bulb oxygenator with carbogen (95% $O_2$ and 5% $CO_2$) was used as a perfusion buffer. The composition of the Tyrode solution was (in mM): NaCl 135; MgCl$_2$×6H$_2$O 1; KCl 5; CaCl$_2$×2H$_2$O 2; NaHCO$_3$ 15; Na$_2$HPO$_4$×2H$_2$O 1; glucose 10; pH 7.3–7.4. The experiments were carried out under constant pressure condition (50 mmHg). After a short prestabilization (10 min) a latex balloon attached through the stainless-steel cannula to a pressure transducer was carefully placed into the left ventricle through the left pulmonary vein and the left atrium. The latex balloon, the cannula and the chamber of the pressure transducer were filled with ethylene glycol/water (1:1) mixture avoiding any air-bubble. The isovolumetric left ventricular pressure was recorded through the pressure transducer. At the beginning of the experiment, the volume of the balloon was adjusted to obtain the end-diastolic pressure of approximately 5 mmHg. Before starting the experiment, the spontaneously beating heart was allowed to stabilise further for 30–50 min with vehicle (0.1% DMSO) in the perfusion buffer.

After 15 min baseline recordings compound of Example 8g (10 μM) was added to the perfusion buffer. The heart was 15 min later exposed to the 8 minute period of global ischemia followed by reperfusion. This procedure was then repeated twice at 35 min intervals. Another series of experiments was performed with vehicle instead of compound of Example 8g. The vehicle concentration (0.1% DMSO) was kept constant throughout the experiments. The baseline value was the average of the two minute recordings obtained just before compound of Example 8g or vehicle was added to the perfusion buffer. The preischemia values were the average of the two minute recordings obtained just before each ischemia period and the reperfusion values were the average of the two minute recordings obtained at 8 min during each reperfusion period.

Figure 3:
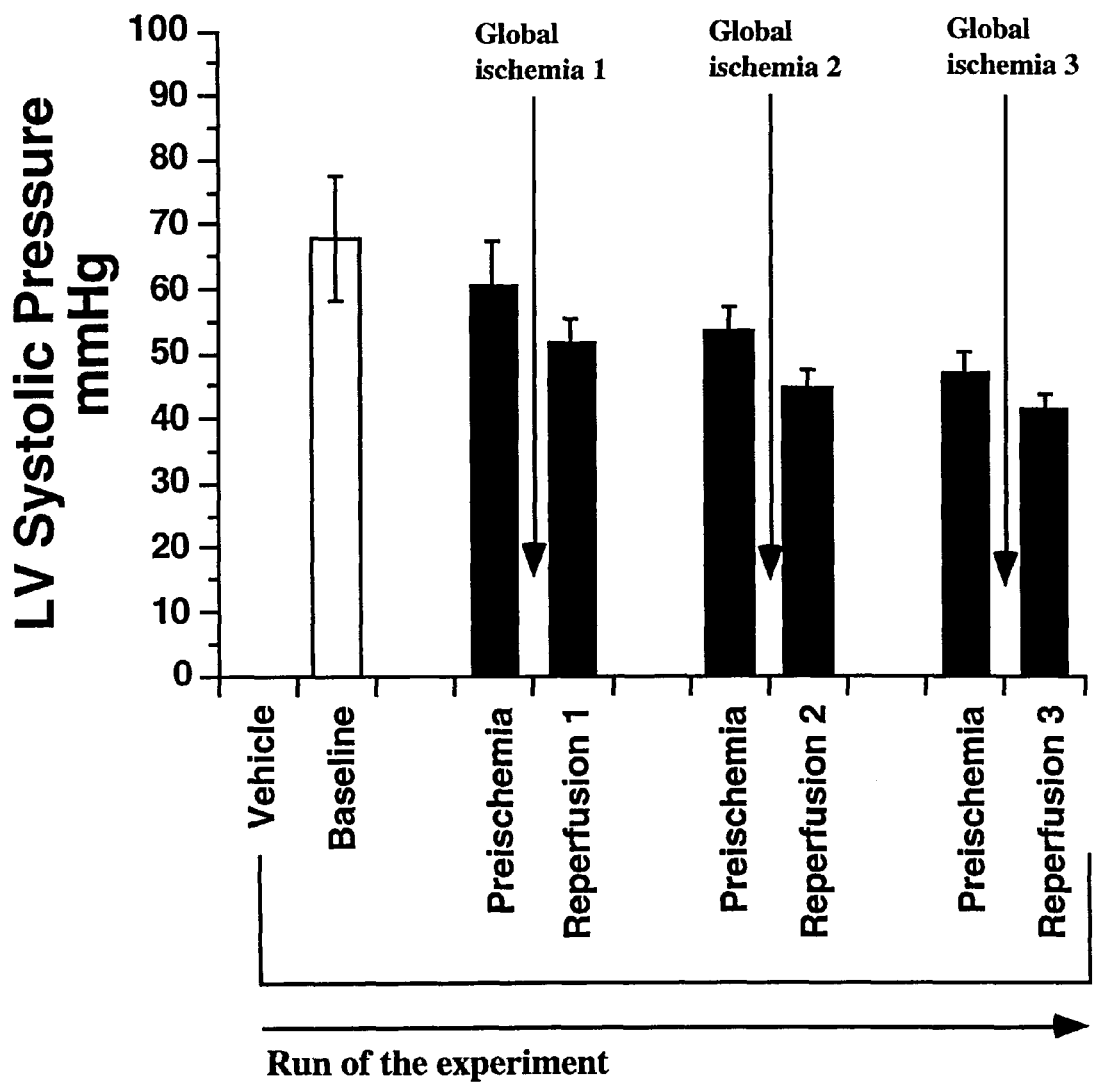
FIG. 3A shows the development of stunned myocardium and the subsequent decrease in the left ventricular systolic pressure.
FIG. 3B shows the complete inhibition of the development of stunned myocardium by the compound of Example 8g.
Figure 3:
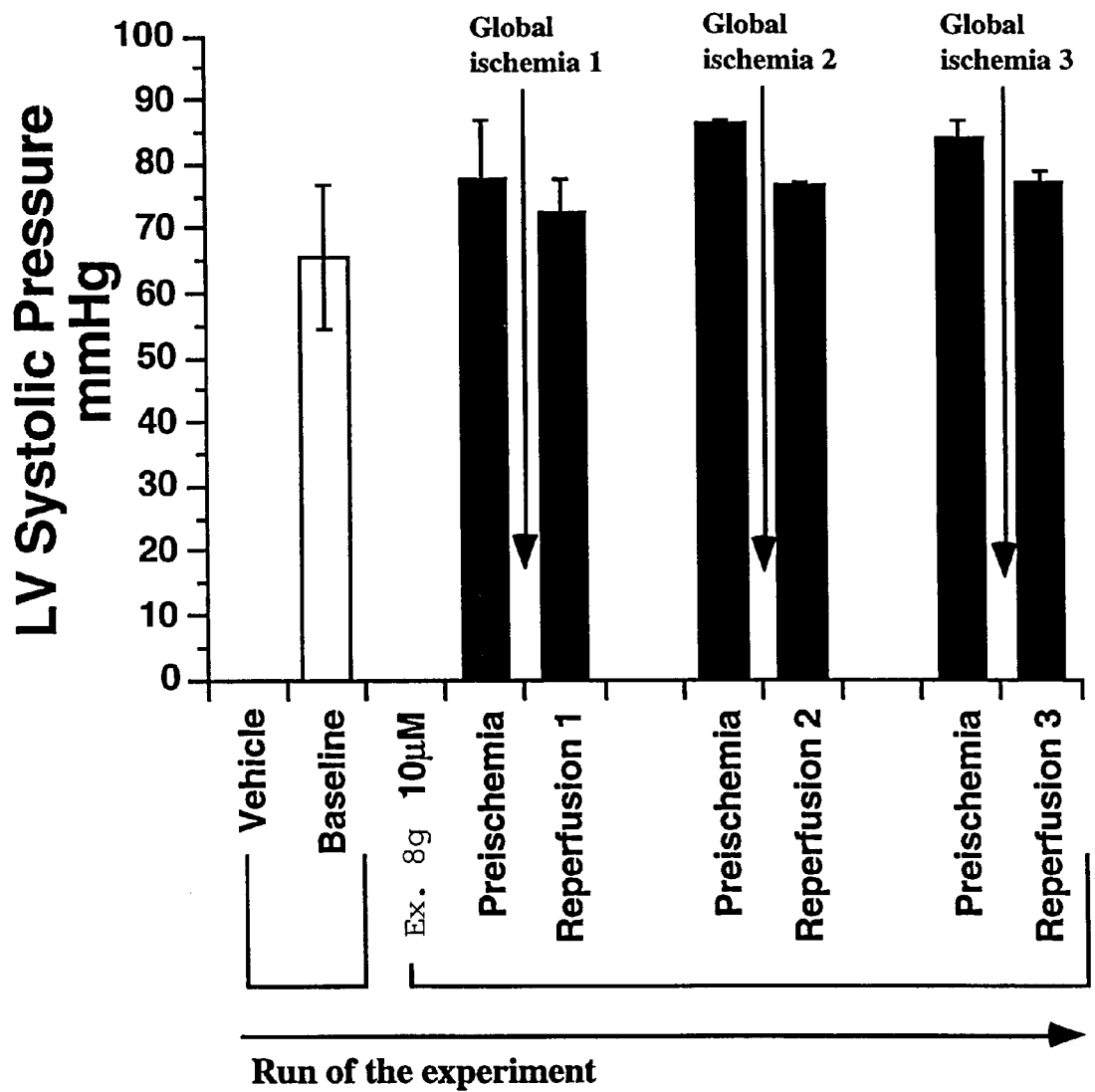

The results are shown in FIGS. 3A and B. FIG. 3A shows the development of stunned myocardium and the subsequent decrease in the left ventricular systolic pressure in the control group. FIG. 3B shows that the phospholamban inhibitor of Example 8g completely inhibited the development of stunned myocardium. Givens are mean ±SEM of 2–3 experiments.

The following non-limiting examples illustrates the preparation of phospholamban inhibitors.

EXAMPLES

Example 1

Preparation of 3-Benzyl-5,7-bis[(1H-tetrazol-5-yl)methoxy]-4-methyl-2H-1-benzopyran-2-one a) 3-Benzyl-5,7-dihydroxy-4-methyl-2H-1-benzopyran-2-one

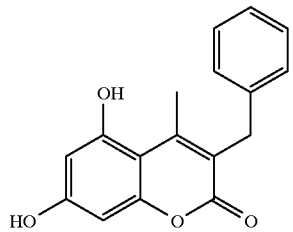

A solution of phloroglucinol dihydrate (20 g) and ethyl 2-benzylacetoacetate (27.5 ml) in ethanol (320 ml) was treated with dry HCl at 0° C. for five hours and the solution was kept at that temperature overnight. The yellow solution was concentrated and triturated with water, the solids filtered, washed with water and dried. The resulting hydrate was thrice evaporated to dryness from toluene, triturated with pethroleum ether (bp. 40–60° C.) and filtered. Yield 33,4 g (96%). Melting point 258–260° C.

$^1$H-NMR (DMSO-d$_6$, 400 MHz): 2.525 (s, 3H, CH$_3$), 3.887 (s, 2H, CH$_2$Ph), 6.171 (d,1H, J=2,4 Hz), 6.274 (d,1H, J=2,4 Hz), 7.167–7.279 (m, 5H, Ph), 10.2 (s, 1H, OH), 10.47 (s, 1H, OH).

b) 3-Benzyl-5,7-bis(cyanomethoxy)-4-methyl-2H-1-benzopyran-2-one

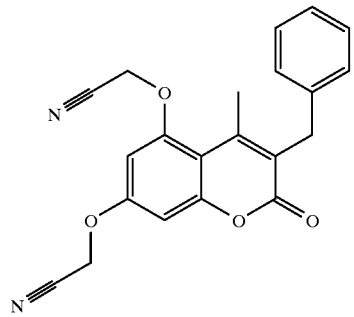

Chloracetonitrile (6.86 g), potassium carbonate (23.9 g) and 12.2 g of the product from example 1a were stirred in 120 ml of DMF at 100° C. under nitrogen for two hours. The reaction mixture was cooled and poured into ice water. The solids were filtered and washed with water. Yield 13.8 g (88%). Melting point 147–154° C.

$^1$H-NMR (DMSO-d$_6$, 400 MHz): 2.525 (s, 3H, CH$_3$), 3.969 (s, 2H, CH$_2$Ph), 5.307 (s, 2H, OCH$_2$CN), 5.314 (s, 2H, OCH$_2$CN), 6.814 (d, 1 H, J=2.5 Hz), 6.940 (d,1H, J=2.5 Hz), 7.18–7.292 (m, 5H, Ph).

c) 3-Benzyl-5,7-bis[(1H-tetrazol-5-yl)methoxy]-4-methyl-2H-1-benzopyran-2-one

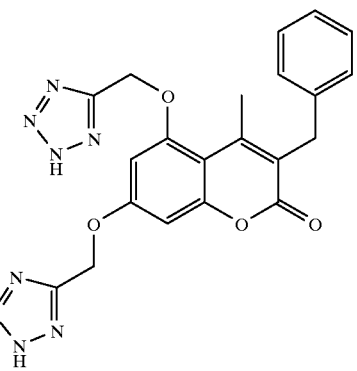

The product from example 1b (1 g), sodium azide (0.42 g) and ammonium chloride (0.34 g) were stirred in DMF (5 ml) under nitrogen at 100° C. for 5 hours. The reaction mixture was allowed to cool down and then poured into ice water. The pH of the solution was adjusted to 10–11 and then the solution either extracted once with ethyl acetate or filtered through CELITE. The solution was acidified to pH 2 with hydrochloric acid, kept at 5° C. and filtered. Yield 0.96 g (81%). Melting point 229–233° C.

$^1$H-NMR (DMSO-d$_6$, 400 MHz): 2.468 (s, 3H, CH$_3$), 3.937 (s, 2H, CH$_2$Ph), 5.596 (s, 2H, OCH$_2$Tet), 5.602 (s, 2H, OCH$_2$Tet), 6.832 (d, 1 H, J=2.4 Hz), 6.851 (d,1H, J=2.4 Hz), 7.171–7.283 (m, 5H, Ph).

Example 2

Preparation of 7,8,9,10-Tetrahydro-1,3-bis[(1H-tetrazol-5-yl)methoxy]-7-phenyl-6H-dibenzo[b,d]pyran-6-one a) 7,8,9,10-Tetrahydro-1,3-dihydroxy-7-phenyl-6H-dibenzo[b,d]pyran-6-one

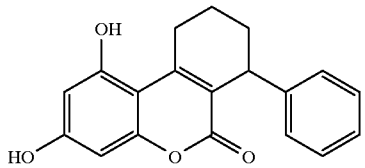

A solution of phloroglucinol (0.7 g) and 2-ethoxycarbonyl-3-phenylcyclohexanone (1,5 g) in ethanol was treated with dry HCl as described in example 1a. The product was first recrystallized from ethanol-water (1:1) and then triturated with ether. Yield 0.61 g.

$^1$H-NMR (DMSO-d$_6$, 400 MHz): 1.38–1.52 (m,1H), 1.57–1.66 (m,1H), 1.69–1.78 (m,1H), 1.86–1.96 (m, 1H), 2.9–3.02 (m,1H), 3.3–3.4 (m,1H), 4.050 (b, 1H), 6.157 (d,1H, J=2.4 Hz), 6.297 (d, 1H, J=2.4Hz), 7.076–7.265 (m, 5H), 10.153 (s, 1H), 10.456 (s, 1H).

b) 7,8,9,10-Tetrahydro-1,3-bis(cyanomethoxy)-7-phenyl-6H-dibenzo[b,d]pyran-6-one

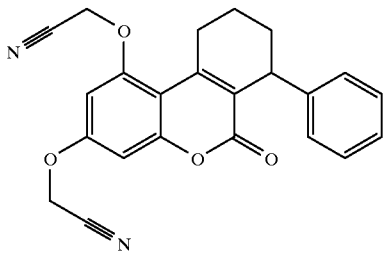

The product from example 2a (0.5 g) was treated with chloroaceto-nitrile (0.25 g) and potassium carbonate (1.12 g) in DMF (5 ml) as described in example 1b. Yield 0.6 g.

$^1$H-NMR (DMSO-$d_6$, 400 MHz): 1.38–1.58 (m, 1H), 1.6–1.7 (m, 1H), 1.7–1.76 (m, 1H), 1.89–1.99 (m, 1H), 2.9–3.03 (m,1H), 3.2–3.28 (m 1H), 4.111 (b,1H), 5.314 (s, 2H), 5.349 (s, 2H), 6.840 (d,1H, J=2.5 Hz), 6.925 (d, 1H, J=2.5 Hz), 7.108–7.274 (m, 5H).

c) 7,8,9,10-Tetrahydro-1,3-bis[(1H -tetrazol-5-yl)methoxy]-7-phenyl-6H-dibenzo[b,d]pyran-6-one

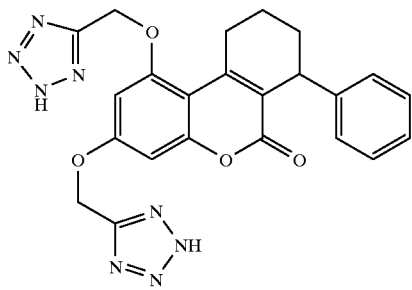

The product from example 2b (0.6 g) was treated with sodium azide (0.2 g) and ammonium chloride (0.17 g) in DMF (5 ml) as in example 1c. The product was recrystallized from a mixture of DMF, ethanol and water (approximately 1:2:3). Yield 0.41 g. Melting point: 153–154° C.

$^1$H-NMR (DMSO-$d_6$, 400 MHz): 1.38–1.5 (m, 1H), 1.5–1.6 (m, 1H), 1.69–1.76 (m, 1H), 1.87–1.96 (m,1H), 2.9–3.05 (m,1H), 3.2–3.3 (m,1H), 4.094 (b, 1H), 5.602 (s, 2H), 5.643 (s, 2H), 6.832 (d, 1H, J=2.3 Hz), 6.851 (d, 1H, J=2.3 Hz), 7.089–7.212 (m, 5H).

Example 3

Preparation of 3-Benzyl-5,7-bis[(2,5-dihydro-5-oxo-4H -1,2,4-oxadiazol-3-yl)-methoxy]-4-methyl-2H -1-benzopyran-2-one a) 3-Benzyl-5,7-bis[(hydroxyamidino)methoxy]-4-methyl-2H-1-benzopyran-2-one

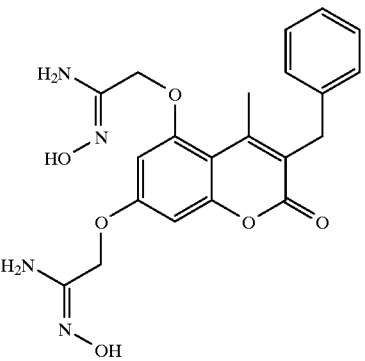

Triethylamine (1.94 ml) was added to a suspension of hydroxylamine hydrochloride (0.97 g) in DMSO (2 ml) and the resulting mixture stirred at room temperature for thirty minutes. The crystals were filtered and washed with THF. The filtrate was concentrated and the product from example 1b (0.5 g) added. This solution was kept at 75° C. overnight. The reaction mixture was treated with ice water, the pH adjusted to 11 and the solids filtered, washed with water, and dried. Yield 0.5 g. Melting point: 155–160° C.

$^1$H-NMR (DMSO-$d_6$, 400 MHz): 2.56 (s, 3H, CH$_3$), 3.938 (s, 2H), 4.466 (s, 2H), 4.486 (s, 2H), 5.565 (s, H, NH$_2$), 5.709 (s, 2H, NH$_2$), 6.658 (d, 1H, J=2.4 Hz), 6.692 (d,1H, J=2.4 Hz), 7.168–7.284 (m, 5H, Ph), 9.346 (s, 1H, OH), 9.362 (s,1H, OH).

b) 3-Benzyl-5,7-bis[(ethoxycarbonyloxyamidino)methoxy]-4-methyl-2H -1-benzopyran-2-one

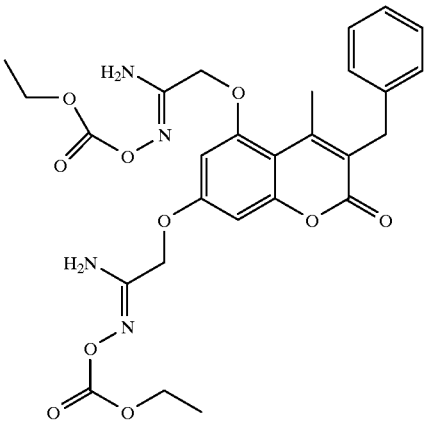

Ethyl chloroformiate (0.45 ml) was added to a solution of the product from example 3a (1 g) and pyridin (0.38 ml) in DMF (5 ml) at 0° C. The reaction mixture was kept at that temperature for an additional 30 minutes and then ice water added. The solids were filtered and washed with water. Yield 1.63 g. Melting point 87–92° C.

$^1$H-NMR (DMSO-$d_6$, 400 MHz): 1.215–1.256 (m, 6H), 2.553 (s, 3H), 3.947 (s, 2H), 4.140–4.198 (m, 4H), 4.566 (s, 2H), 4.599 (s, 2H), 6.688 (d, 1H, J=2.4 Hz), 6.718 (d, 1H, J=2.4 Hz), 6.792 (b, 2H, NH$_2$), 6.818 (b, 2H, NH$_2$), 7.171–7.285 (m, 5H).

c) 3-Benzyl-5,7-bis[(2,5-dihydro-5-oxo-4H -1,2,4-oxadiazol-3-yl)-methoxy]-4-methyl-2H -1-benzopyran-2-one

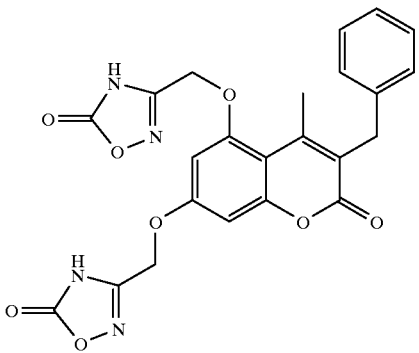

The product from the previous example (1.5 g) and DBU (0.8 ml) in DMF (5 ml) was stirred at room temperature overnight. The reaction mixture was treated with ice water and acidified. The solids were filtered and washed with water. The resulting solid mass was taken in 0.1 N sodium hydroxide solution, treated with activated carbon and finally acidified. Yield 0.64 g. Melting point: 130–136° C.

$^1$H-NMR (DMSO-d$_6$, 400 MHz): 2.524 (s, 3H), 3.954 (s, 2H), 5.187 (s, 2H), 5.215 (s, 2H), 6.748 (d, 1H, J=2.4 Hz), 6.834 (d, 1H, J=2.4 Hz), 7.158–7.289 (m, 5H), 12.8 (b, 2H).

Example 4

Preparation of 7,8,9,10-Tetrahydro-bis[(1H-tetrazol-5-yl)methoxy]-1,3-dihydroxy-6H-dibenzo[b,d]pyran-6-one a) 7,8,9,10-Tetrahydro-1,3-dihydroxy-6H-dibenzo[b,d]pyran-6-one

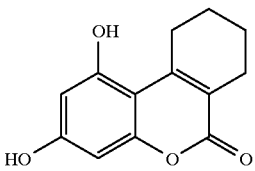

Phloroglucinol (1 g) and ethyl 2-oxocyclohexane carboxylate (1.32 g) were stirred in 75% sulfuric acid (10 ml) overnight, the mixture poured into ice water and filtered. Yield: 1.55 g.

$^1$H-NMR (DMSO-d$_6$, 400 MHz): 1.65 (b, 4H), 2.345 (b, 2H), 3.037 (b, 2H), 6.138 (d, 1H, J=2.4 Hz), 6.245 (d, 1H, J=2.4 Hz), 10.069 (b,1H, OH), 10.322 (s,1H, OH).

b) 7,8,9,10-Tetrahydro-bis(cyanomethoxy)-1,3-dihydroxy-6H-dibenzo[b,d]pyran-6-one

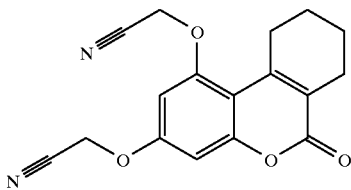

The product from the previous example (0.5 g), chloroacetonitrile (0.34 g) and potassium carbonate (1.5 g) in DMF (5 ml) were reacted as in example 1b. Yield: 0.44 g.

$^1$H-NMR (DMSO-d$_6$, 400 MHz): 1.68 (b, 4H), 2.41 (b, 2H), 3.00 (b, 2H), 5.297 (s, 2H), 5.309 (s, 2H), 6.797 (d, 1H, J=2.4 Hz), 6.899 (d, 1H, J=2.4 Hz).

c) 7,8,9,10-Tetrahydro-bis[(1H-tetrazol-5-yl)methoxy]-1,3-dihydroxy-6H-dibenzo[b,d]pyran-6-one

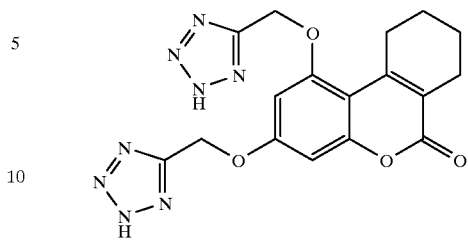

The product from the previous example (0.4 g) was treated with sodium azide (0.18 g) and ammonium chloride (0.14 g) in DMF (2.5 ml) as in example 1c. The product was recrystallized from ethanol-DMF (1:1). Yield 0.17 g. Melting point 283–286° C.

$^1$H-NMR (DMSO-d$_6$, 400 MHz): 1.626 (b, 4H), 2.393 (b, 2H), 2.971 (b, 2H), 5.583 (s, 2H), 5.599 (s, 2H), 6.811 (s, 2H).

Example 5

Preparation of 5,7-Bis[(1H-tetrazol-5-yl)methoxy]-4-phenyl-2H-1-benzopyran-2-one a) 5,7-Dihydroxy-4-phenyl-2H-1-benzopyran-2-one

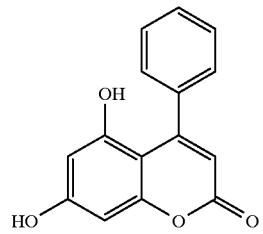

A solution of phloroglucinol (2.00 g) and ethyl benzoylacetate (3.05 g) in ethanol (30 ml) was treated with dry HCl as described in example 1a. The product was recrystallized from ethanol-water (1:1). Yield 3.0 g (75%).

$^1$H-NMR (DMSO-d$_6$, 300 MHz): 5.739 (s, 1H, CH=C), 6.155 (d, 1H, J=2.3 Hz), 6.263 (d, 1H, J=2.3 Hz), 7.305–7.381 (m, 5H, Ph), 10.084 (s, 1H, OH), 10.368 (s,1H, OH).

b) 5,7-Bis(cyanomethoxy)-4-phenyl-2H-1-benzopyran-2-one

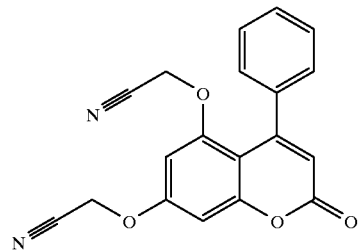

The product from previous example (1.00 g) was treated with chloroaceto-nitrile (0.62 g) and potassium carbonate (2.72 g) in DMF (5 ml) as described in example 1b. The reaction mixture was poured into ice water and the mixture extracted with ethyl acetate. Ethyl acetate was washed with 1 M NaOH, dried with sodium sulfate and evaporated. The product was recrystallized from isopropanol. Yield 0.41 g (31%).

¹H-NMR (DMSO-d₆, 300 MHz): 4.845 (s, 2H, OCH₂CN), 5.344 (s, 2H, OCH₂CN), 6.086 (s, 1H, CH=C), 6.770 (d, 1H, J=2.4 Hz), 7.040 (d, 1H, J=2.4 Hz), 7.320–7.443 (m, 5H, Ph).

c) 5,7-Bis[(1H-tetrazol-5-yl)methoxy]-4-phenyl-2H-1-benzopyran-2-one

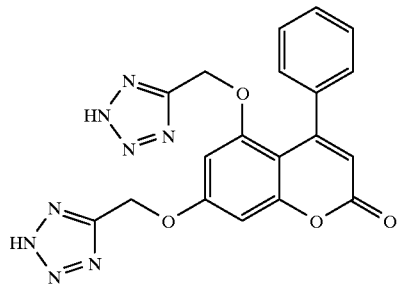

The product from previous example (0.40 g) was treated with sodium azide (0.16 g) and ammonium chloride (0.14 g) in DMF (2 ml) at 100° C. for 2 hours. The product was isolated as described in example 1c. Yield: 0.40 g (79%). Melting point 222–224° C.

¹H-NMR (DMSO-d₆, 400 MHz): 5.148 (s, 2H, OCH₂Tet), 5.649 (s, 2H, OCH₂Tet), 5.968 (s, 1H, CH=C), 6.811 (d, 1H, J=2.3 Hz), 6.962 (d, 1H, J=2.3 Hz), 6.994–7.185 (m, 5H, Ph).

Example 6

Preparation of 7,8,9,10-Tetrahydro-1,3-bis[(1H-tetrazol-5-yl)methoxy]-8-phenyl-6H-dibenzo[b,d]pyran-6-one a) 7,8,9,10-Tetrahydro-1,3-dihydroxy-8-phenyl-6H-dibenzo[b,d]pyran-6-one

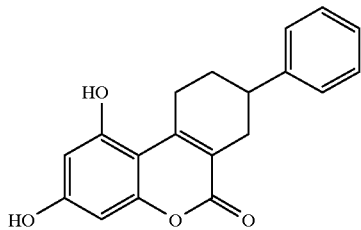

A solution of phloroglucinol (1.56 g) and ethyl 2-oxo-5-phenylcyclo-hexane-carboxylate (2.52 g) in ethanol (25 ml) was treated with dry HCl as described in example 1a. The precipitate was filtered and washed with water and EtOH. Yield 1.0 g (32%).

¹H-NMR (DMSO-d₆, 400 MHz): 1.72–1.82 (m,1H), 2.01 (b,1H), 2.317–2.387 (m, 1H), 2,707–2,763 (m, 1H), 2,830 (b, 1H), 3,041 (b, 1H), 3.35 and 3.40 (b, 1H), 6.174 (d, 1H, J=2.3 Hz), 6.277 (d, 1H, J=2.3 Hz), 7.200–7.350 (m, 5H, Ph), 10.131 (s, 1H, OH), 10.401 (s, 1H, OH).

b) 7,8,9,10-Tetrahydro-1,3-bis(cyanomethoxy)-8-phenyl-6H-dibenzo[b,d]pyran-6-one

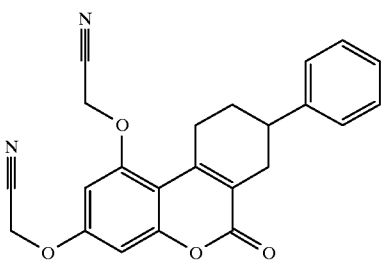

The product from previous example (1.0 g) was treated with chloroacetonitrile (0.57 g) and potassium carbonate (1.0 g) in DMF (5 ml) as described in example 1b. DMF was evaporated and residue dissolved in EtOAc. Ethyl acetate was washed with 1 M NaOH, dried with sodium sulfate and evaporated. The product was recrystallized from acetone-isopropanol (1:3). Yield 0.50 g (40%).

¹H-NMR (DMSO-d₆, 300 MHz): 1.75–1.88 (m, 1H), 2.05 (b, 1H), 2.38–2.48 (m,1H), 2.77–2.85 (m,1H), 2.90 (b, 1H), 3.07 (b, 1H), 3.22 and 3.28 (b, 1H), 5.316 (s, 2H, OCH₂CN), 5.331(s, 2H, OCH₂CN), 6.829 (d, 1H, J=2.5 Hz), 6.939 (d, 1H, J=2.5 Hz), 7.210–7.380 (m, 5H, Ph).

c) 7,8,9,10-Tetrahydro-1,3-bis[(1H-tetrazol-5-yl)methoxy]-8-phenyl-6H-dibenzo[b,d]pyran-6-one

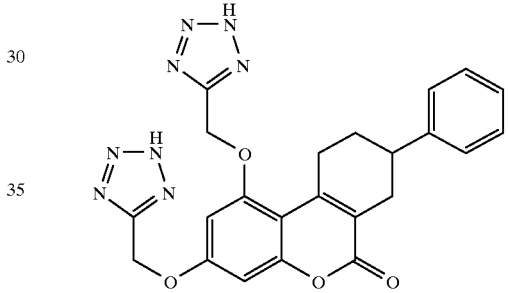

The product from previous example (0.30 g) was treated with sodium azide (0.10 g) and ammonium chloride (0.09 g) in DMF (2 ml) at 100° C. for 3.5 hours. The product was isolated in the same manner as in example 1c. Yield 0.30 g (82%). Melting point 235–245° C.

¹H-NMR (DMSO-d₆, 400 MHz): 1.70–1.80 (m, 1H), 1.96 (b, 1H), 2.38–2.446 (m, 1H), 2.836 (m, 2H), 3.052 (b, 1H), 3.252 and 3.301(b, 1H), 5.604 (s, 2H, OCH₂CN), 5.632 (s, 2H, OCH₂CN), 6.827 (d, 1H, J=2.5 Hz), 6.858 (d, 1H, J=2.5 Hz), 7.209–7.351(m, 5H, Ph).

Example 7

Preparation of 5,7-Bis[(1H-tetrazol-5-yl)methoxy]-4-methyl-3-(2-phenylethyl)-2H-1benzopyran-2-one a) 5,7-Dihydroxy-4-methyl-3-(2-phenylethyl)-2H-1-benzopyran-2-one

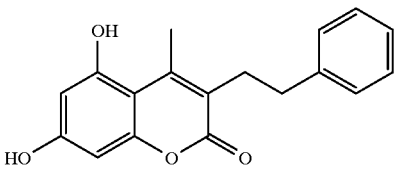

A solution of phloroglucinol (0.87 g) and ethyl 2-(2-phenylethyl)acetoacetate (1.62 g) in ethanol (30 ml) was treated with dry HCl as described in example 1a. Yield: 1.77 g (87%). Melting point 248–252° C.

$^1$H-NMR (DMSO-d$_6$, 300 MHz): 2.413 (s, 3H, CH$_3$), 2.652–2.782 (m, 4H, CH$_2$CH$_2$), 6.151(d, 1H, J=2.4 Hz), 6.256 (d, 1H, J=2.4 Hz), 7.183–7.304 (m, 5H, Ph), 10.137 (s, 1H, OH), 10.369 (s, 1H, OH).

b) 5,7-Bis(cyanomethoxy)-4-methyl-3-(2-phenylethyl)-2H-1-benzopyran-2-one

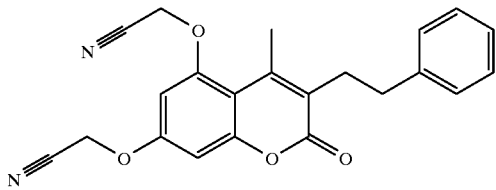

The product from previous example (0.90 g) was treated with chloroacetonitrile (0.48 g) and potassium carbonate (2.1 g) in DMF (5 ml) at 100° C. for 0.5 hours. The product was isolated as described in example 1b. Yield 1.00 g (88%). Melting point 179–183° C.

$^1$H-NMR (DMSO-d$_6$, 300 MHz): 2,384 (s, 3H, CH$_3$), 2.699–2,754 (m, 2H, CH$_2$CH$_2$), 2.805–2.841(m, 2H, CH$_2$CH$_2$), 5,302 (s, 4H, OCH$_2$CN), 6,790 (d, 1H, J=2.5 Hz), 6.909 (d, 1H, J=2.5 Hz), 7.190–7.307 (m, 5H, Ph).

c) 5,7-Bis[(1H-tetrazol-5-yl)methoxy]-4-methyl-3-(2-phenylethyl)-2H-1benzopyran-2-one

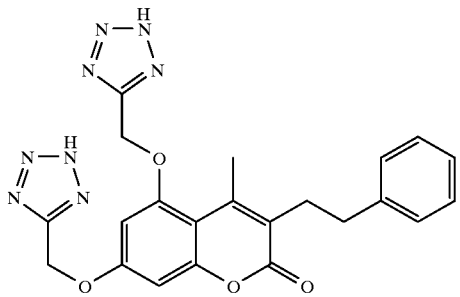

The product from previous example (0.40 g) was treated with sodium azide (0.15 g) and ammonium chloride (0.12 g) in DMF (2 ml) at 100° C. for 2.5 hours. The product was isolated as described in example 1c. Yield 0.385 g (78%). Melting point 248–250° C.

$^1$H-NMR (DMSO-d$_6$, 400 MHz): 2.368 (s, 3H, CH$_3$), 2.668–2.707 (m, 2H, CH$_2$CH$_2$), 2.783–2.822 (m, 2H, CH$_2$CH$_2$), 5.593 (s, 2H, OCH$_2$Tet), 5.604 (s, 2H, OCH$_2$Tet), 6.819 (d, 1H, J=2.3 Hz), 6.834 (d, 1H, J=2.3 Hz), 7.161–7.291(m, 5H, Ph).

Example 8

Preparation of 5,7-Bis[(1H-tetrazol-5-yl)methoxy]-1,3-dibenzyl-4-methyl-2(1H)-quinolinone a) 2-Benzyl-3-oxobutanoic acid 3,5-dimethoxyanilid

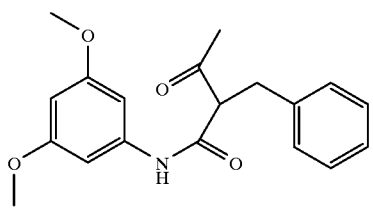

3,5-Dimethoxyaniline (5 g) was added in portions to a preheated (160° C.) ethyl 2-benzyl acetoacetate (15 ml) under nitrogen and kept at that temperature for 60 minutes. The cooled solution was diluted with heptane-ethyl ether and filtered. Yield 5.2 g (49%).

$^1$-H-NMR (DMSO-d$_6$, 300 MHz): 2.183 (s, 3H), 3.069 (d, 2H, J=7.2 Hz), 3.923 (t, 1H, J=7.2 Hz), 6.616 (dd. 1H, J=2.3 Hz), 6.765 (d, 2H, J=2.3 Hz), 7.13–7.3 (m, 5H), 10.123 (s, 1H).

b) 3-Benzyl-5,7-dimethoxy-4-methyl-2(1H)-quinolinone

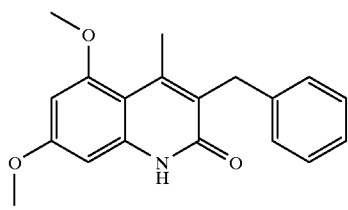

The product from the previous example (1.2 g) was added to a preheated (85° C.) methanesulfonic acid (3.5 ml) and kept at that temperature for 15 minutes. The solution was allowed to cool and then treated with ice water. The product was filtered, washed with sodium bicarbonate and water. Yield 1.08 g (95%).

$^1$-H-NMR (300 MHz):2.486 (s, 3H), 3.785 (s, 3H), 3.808 (s, 3H), 3.985 (s, 2H), 6.315 (d, 1H, J=2.4 Hz), 6.472 (d, 1H, J=2.4 Hz), 7.1–7.3 (m, 5H), 11.52 (s, 1H).

c) 3-Benzyl-5,7-dihydroxy-4-methyl-2(1H)-quinolinone

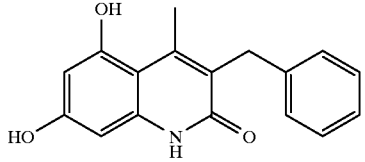

The product from the previous example (1g) was refluxed under nitrogen in pyridine hydrochloride (5 g) for twenty minutes. The reaction mixture was treated with water and the product filtered. Yield 0.9 g (100%). Melting point: 307–312° C.

$^1$-H-NMR (300 MHz):2.503 (s, 3H), 3.942 (s, 2H), 6.102 (d, 1H, J=2.3 Hz), 6.187 (d, 1H, J=2.3 Hz), 7.1–7.25 (m, 5H), 9.725 (s, 1H), 9.984 (s, 1H), 11.285 (s, 1H).

d) 1,3-Dibenzyl-5,7-dimethoxy-4-methyl-2(1H)-quinolinone

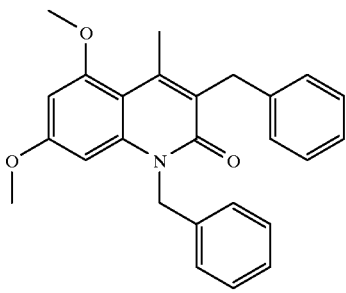

The product from the example 8b (1g), potassium t-butoxide (0.62 g) and benzyl bromide (0.68 ml) were stirred in DMSO (10 ml) at 60° C. for 4 hours. The reaction mixture was treated with water, extracted with toluene and evaporated. The product was triturated with ethyl ether and filtered. Yield 0.5 g (39%).

$^1$-H-NMR (400 MHz):2.537 (s, 3H), 3.708 (s, 3H), 3.826 (s, 3H), 4.124 (s, 2H), 5.56 (b, 2H), 6.413–6.434 (m, 2H), 7.154–7.332 (m, 10H).

e) 1,3-Dibenzyl-5,7-dihydroxy-4-methyl-2(1H)-quinolinone.

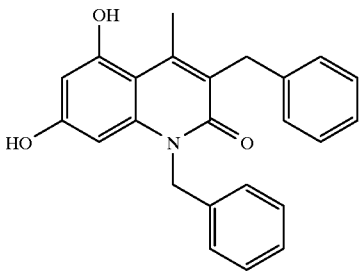

The product from the previous example (2 g) was treated with pyridine hydrochloride (10 g) as described in example 8c. The product was extracted with ethyl acetate and evaporated. Yield 1,4 g (75%).

$^1$-H-NMR (400 MHz):2.570 (s, 3H), 4.076 (s, 2H), 5.450 (b, 2H), 6.135 (d, 1H, J=2.2 Hz), 6.199 (d, 1H, J=2.2 Hz), 7.128–7.333 (m, 10H), 9.83 (b, 1H), 10.166 (s, 1H).

f) 5,7-Bis(cyanomethoxy)-1,3-dibenzyl-4-methyl-2(1H)-quinolinone.

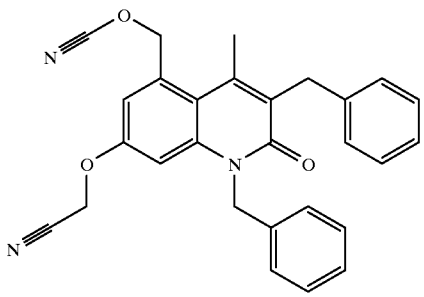

The product from the previous example (1.4 g) was treated with chloroacetonitrile (0.76 g) and K$_2$CO$_3$ (2.5 g) in DMF (20 ml) as described in example 1b. Yield 1.5 g (89%).

$^1$-H-NMR (400 MHz):2.555 (s, 3H), 4.146 (s, 2H), 5.214 (s, 2H), 5.275 (s, 2H), 5.578 (s, 2H), 6.735 (s, 2H), 7.13–7.33 (m, 10H).

g) 5,7-Bis[(1H-tetrazol-5-yl)methoxy]-1,3-dibenzyl-4-methyl-2(1H)-quinolinone.

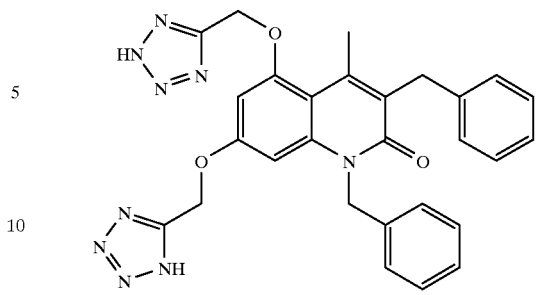

The product from the previous example (1.3 g) was treated with sodium azide (0.41g) and ammonium chloride (0.34 g) as described in example 1c. Yield: 0.69 g (45%).

$^1$-H-NMR (400 MHz):2.471(s, 3H), 4.113 (s, 2H), 5.477 (s, 2H), 5.55 (b, 2H), 5.574 (s, 2H), 6.670 (d, 1H, J=2.1 Hz), 6.775 (d, 1H, J=2.1 Hz), 7.13–7.32 (m, 10H).

Example 9

Preparation of 5,7-Bis[(1H-tetrazol-5-yl)methoxy]-3-benzyl-1,4-dimethyl-2(1H)-quinolinone.

a) 3-Benzyl-5,7-dimethoxy-1,4-dimethyl-2(1H)-quinolinone.

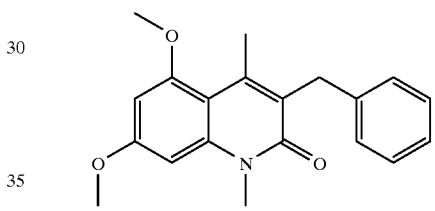

The product from example 8b (0.5 g), t-BuOK (0.2 g) and methyl iodide (0.4 ml) were stirred in DMSO (5 ml) at 35° C. for two days. The reaction mixture was treated with water and extracted with toluene. The product was purified by column chromatography using toluene-ethyl acetate-acetic acid 8:2:1 as the eluent. Yield 0.24 g (46%).

$^1$-H-NMR (300 MHz):2.51(s, 3H), 3.632 (s, 2H), 3.846 (s, 3H), 3.896 (s, 3H), 4.047 (s, 2H), 6.468 (d, 1H, J=2.3 Hz), 6.558 (d, 1H, J=2.3 Hz), 7.1–7.26 (m, 5H).

b) 3-Benzyl-5,7-dihydroxy-1,4-dimethyl-2(1H)-quinolinone.

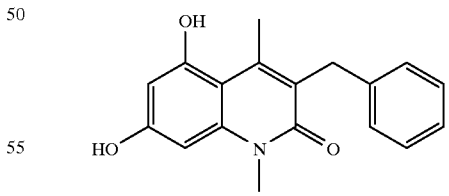

The product from the previous example (0.2 g) was treated with pyridine hydrochloride (2 g) as described in example 8c and the product extracted with ethyl acetate. Yield 0.16 g (89%).

$^1$-H-NMR (400 MHz):2.567 (s, 3H), 3.515 (s, 3H), 4.005 (s, 2H), 6.244 (d, 1H, J=2.3 Hz), 6.268 (d, 1H, J=2.3 Hz), 7.08–7.25 (m. 5H), 9.879 (s, 1H), 10.113 (s,1H).

c) 5,7-Bis(cyanomethoxy)-3-benzyl-1,4-dimethyl-2(1H)-quinolinone.

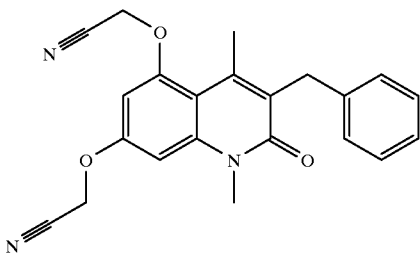

The product from the previous example (0.15 g), chloroacetonitrile 0.08 g) and $K_2CO_3$ (0.28 g) were reacted in DMF (2 ml) as described in example 1b. Yield 0.16 g (84%).

$^1$-H-NMR (400 MHz): 2.524 (s, 3H), 3.658 (s, 3H), 4.079 (s, 2H), 5.292 (s, 2H), 5.379 (s, 2H), 6.766 (d, 1H, J=2.3 Hz), 6.855 (d, 1H, J=2.3 Hz), 7.13–7.24 (m 5H).

d) 5,7-Bis[(1H-tetrazol-5-yl)methoxy]-3-benzyl-1,4-dimethyl-2(1H)-quinolinone.

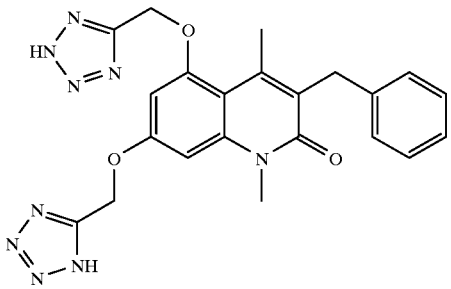

The product from the previous example (0.15 g) was treated with $NaN_3$ (57 mg) and $NH_4Cl$ (47 mg) in DMF (2 ml) as described in example 1c. Yield 0.115 g. Melting point: 250–253° C.

$^1$-H-NMR (400 MHz): 2.451(s, 3H), 3.649 (s, 3H), 4.042 (s, 2H), 6.792 (d, 1H, J=2.2 Hz), 6.833 (d,1H, J=Hz), 7.1–7.25 (m, 5H).

Example 10

Preparation of 3-Benzyl-5,7-bis[(2-methyl-1H-tetrazol-5-yl)methoxy]-4-methyl-2H -1-benzopyran-2-one and the three isomers.

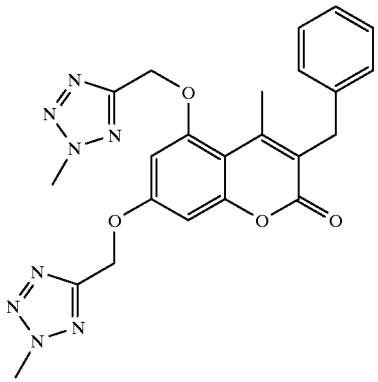

0.07 ml of methyl iodide was added to a solution of 0.2 g of the product from example 1c and 0.31 g of $K_2CO_3$ in 2 ml of DMF and the mixture stirred at room temperature for 4 hours. The reaction mixture was poured into ice water and filtered. Yield 0.2 g as a mixture of four regioisomers, melting point 71–76° C.

$^1$H-NMR (DMSO-$d_6$, 400 MHz): 2.47 (s, $CH_3$), 2.48 (s, $CH_3$), 3.93 (s, $CH_2$Ph), 4.11(s, $NCH_3$), 4.12 (s, $NCH_3$), 4.15 (s, $NCH_3$), 4.38 (s, $NCH_3$), 4.40 (s, $NCH_3$), 5.51(s, $OCH_2$), 5.52 (s, $OCH_2$), 5.62 (s, $OCH_2$), 5.67 (s, $OCH_2$), 6.84–6.91 (m, 2H), 7.16–7.28 (m,5H, Ph).

Example 11

Preparation of 3-Benzyl-5,7-bis[1-(1H-tetrazol-5-yl) ethoxy]4-methyl-2H-1-benzopyran-2-one, mixture of stereoisomers a) 3-Benzyl-5,7-bis-[(1-cyano)ethoxy)-4-methyl-2H -1-benzopyran-2-one

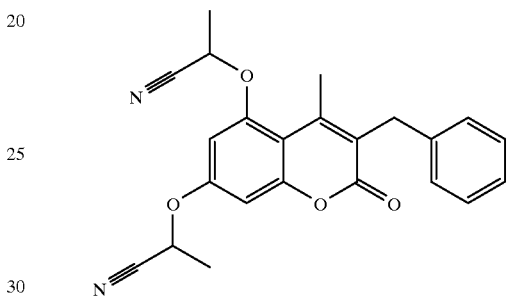

The product from example 1a (1 g), 2-chlorpropionitrile (0.7 g) and potassium carbonate (2 g) were heated in DMF (15 ml) under nitrogen at 110° C. for sixty minutes. The mixture was treated with water, filtered and washed with 1 N NaOH and water. Yield 1.2 g.

$^1$H-NMR (DMSO-$d_6$, 300 MHz): 1.74–1.78 (t+t, 6 H, CH-$CH_3$), 2.53 (s, 3 H), 3.97 (s, 2H), 5.58–5.66 (m, 2H, CH-$CH_3$), 6.87 (m, 1H), 6.99 (d, 1H), 7.18–7.31(m, 5H).

b) 3-Benzyl-5,7-bis[1-(1H -tetrazol-5-yl)ethoxy]4-methyl-2H-1-benzopyran-2-one, mixture of stereoisomers.

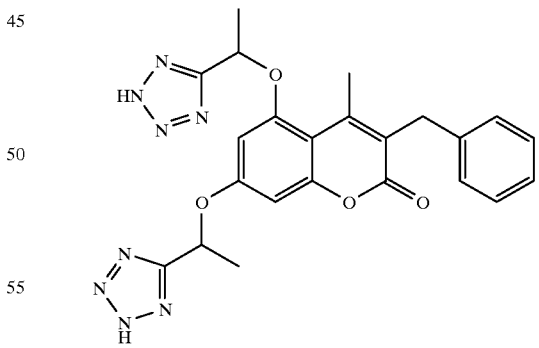

The product from the previous example (0.5 g), sodium azide (0.18 g) and ammonium chloride (0.15 g) were heated in DMF (7 ml) at 100° C. for 90 minutes. The product was treated with water, extracted with ethyl acetate and evaporated. Yield 0.57 g. Melting point 91–104° C.

$^1$H-NMR (DMSO-$d_6$, 300 MHz): 1.69–1.77 (m, 6H, CH-$CH_3$), 2.54 (s, 3H), 3.94 (s, 2H), 6.10–6.17 ((m, 2H, CH-$CH_3$), 6.65 (dd, 1H), 6.74 (dd, 1H), 7.13–7.30 (m, 5H).

Example 12

Preparation of 5,7-Bis(carboxymethoxy)-1,3-dibenzyl-4-methyl-2(1H)-quinolinone

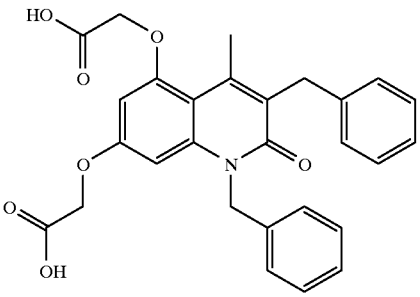

The product from example 8f (0.2 g) was refluxed in a solution of concentrated hydrochloric acid (3 ml) and acetic acid (2 ml) for one hour. The product was filtered at 25° C. Yield 0.14 g.

$^1$H-NMR (300 Mhz, DMSO-$d_6$): 2.63 (s, $CH_3$), 4.14 (s, 2H, $CH_2$Ph), 4.66 (s, 2 H, $OCH_2$COOH), 4.79 (s, 2H, $OCH_2$COOH), 5.53 (s, 2H, $NCH_2$Ph), 6.41(d, 1H, J=2.2 Hz), 6.45 (d, 1H, J=2.2 Hz), 7.13–7.34 (m, 10H, Ph).

Example 13

Preparation of 3-Benzyl-5,7-bis[(1H-tetrazol-5-yl)methoxy]-1-(4-fluorobenzyl)-4-methyl-2(1H)-quinolinone a) 1-Benzyl-5,7-dimethoxy-3-(4-fluorobenzyl)-4-methyl-2(1H)-quinolinone

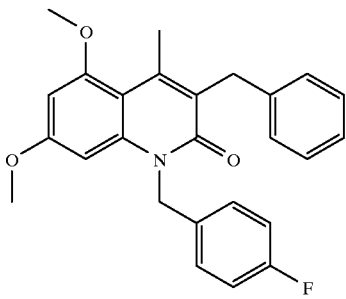

The product from example 8b (2 g), potassium -tert-butoxide (0.87 g) and 4-fluorobenzylchloride (1.12 g) were heated in DMSO (20 ml) at 60° C. for three hours as in example 8d. Yield 1.28 g.

$^1$H-NMR (400 Mhz, DMSO-$d_6$): 2.53 (s, 3H), 3.73 (s, 3H), 3.83 (s, 3H), 5.55 (s, 2H), 6.43 (s, 2H), 7.12–7.2 (m, 5H), 7.26–7.28 (m, 4H).

b) 3-Benzyl-5,7-dihydroxy-1-(4-fluorobenzyl)-4-methyl-2(1H)-quinolinone

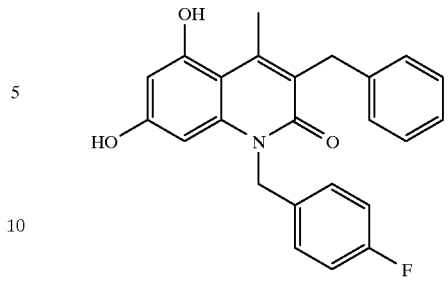

The product from previous example (1.25 g) were heated in pyridine hydrochloride (12.5 g) at about 225° C. for 9 minutes. Yield 1 g.

$^1$H-NMR (300 Mhz, DMSO-$d_6$): 2.56 (s, 3H), 4.07 (s, 2H), 5.4 (b, 2H), 6.13 (d, 1H, J=2.1 Hz), 6.20 (d, 1H, J=2.1 Hz), 7.12–7.28 (m, 9H), 9.88 (s, 1H),10.22(s,1H).

c) 3-Benzyl-5,7-Bis(cyanomethoxy)-1-(4-fluorobenzyl)-4-methyl-2(1H)-quinolinone

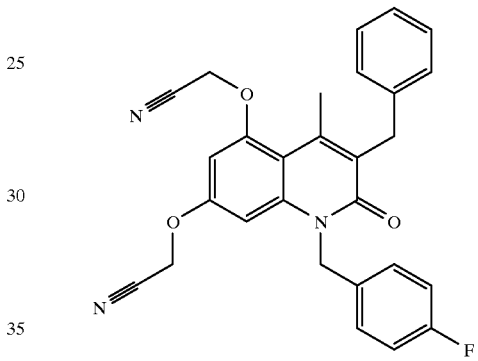

The product from the previous example (1 g), $ClCH_2CN$ (0.43 g) and $K_2CO_3$ (1.42 g) were heated in DMF (8 ml) at 120° C. for one hour. Yield 0.94 g.

$^1$H-NMR (300 Mhz, DMSO-$d_6$): 2.55 (s, 3H), 4.14 (s, 2H), 5.25 (s, 2H), 5.28 (s, 2H), 5.57 (s, 2H), 6.74 (s, 2H, ArH), 7.1–7.3 (m, 9H).

d) 3-Benzyl-5,7-bis[(1H-tetrazol-5-yl)methoxy]-1-(4-fluorobenzyl)-4-methyl-2(1H)-quinolinone

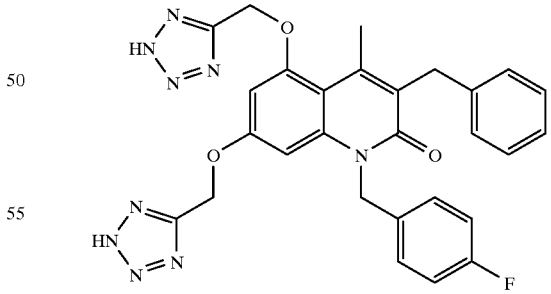

The product from the previous example (0.5 g), sodium azide (0.14 g) and ammonium chloride (0.12 g) were heated in DMF (5 ml) at 120° C. for 90 min. The product was triturated with acetonitrile. Yield 0.28 g. Melting point: 126–132° C.

$^1$H-NMR (300 Mhz, DMSO-$d_6$): 2.48 (s, 3H), 4.11(s, 2H), 5.51(s, 2H), 5.55 (s, 2H), 5.58 (s, 2H), 6.67 (d, 1H, J=2.1 Hz), 6.78 (d, 1H, J=2.1 Hz).

Example 14

Preparation of 5,7-Bis[(1H-tetrazol-5-yl)methoxy]-3-(4-chlorobenzyl)-4-methyl-2H-1-benzopyran-2-one a) 3-(4-Chlorobenzyl)-5,7-dihydroxy-4-methyl-2H-1-benzopyran-2-one

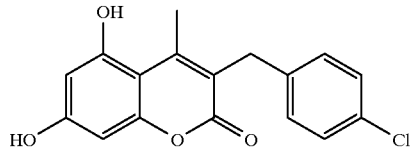

A solution of phloroglucinol (1.57 g) and ethyl 2-(4-chlorobenzyl)-acetoacetate (3.18 g) in ethanol (25 ml) was treated with dry HCl at 0° C. for 1.5 hours and the solution was kept at that temperature overnight. Solvent was evaporated and the precipitate triturated with water. Yield 3.87 g (98%). Melting point 270–278° C.

$^1$H-NMR (DMSO-$d_6$, 300 MHz): 2.52 (s, 3H, CH$_3$), 3.87 (s, 2H, CH$_2$), 6.17 (d, 1H, J=2.4 Hz), 6.28 (d, 1H, J=2.4 Hz), 7.18–7.34 (m, 4H, Ph), 10.21(s, 1H, OH), 10.48 (s, 1H, OH).

b) 5,7-Bis(cyanomethoxy)-3-(4-chlorobenzyl)-4-methyl-2H-1-benzopyran-2-one

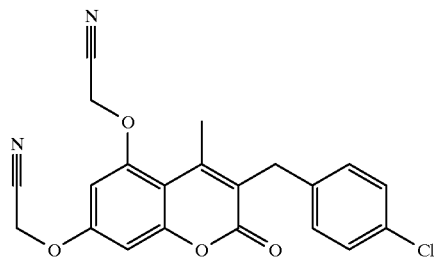

The product from the previous example (1.00 g), chloroacetonitrile (0.50 g) and potassium carbonate (2.18 g) were heated in DMF (5 ml) at 100° C. for 30 minutes. The product was isolated as described in example 1b. Yield 0.90 g (72%).

$^1$H-NMR (DMSO-$d_6$, 300 MHz): 2.52 (s, 3H, CH$_3$), 3.95 (s, 2H, CH$_2$), 5.308 (s, 2H, OCH$_2$CN), 5.312 (s, 2H, OCH$_2$CN), 6.81(d, 1H, J=2.5 Hz), 6.94 (d, 1H, J=2.5 Hz), 7.22–7.33 (m, 4H, Ph).

c) 5,7-Bis[(1H-tetrazol-5-yl)methoxy]-3-(4-chlorobenzyl)-4-methyl-2H-1-benzopyran-2-one

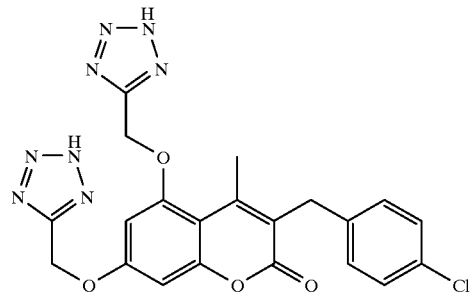

The product from the previous example (0.40 g), sodium azide (0.14 g) and ammonium chloride (0.11 g) were heated in DMF (2 ml) at 100° C. for 2 hours. The product was isolated as in example 1c. Yield 0.40 g (82%).

$^1$H-NMR (DMSO-$d_6$, 300 MHz): 2.46 (s, 3H, CH$_3$), 3.92 (s, 2H, CH$_2$), 5.602 (s, 2H, OCH$_2$Tet), 5.609 (s, 2H, OCH$_2$Tet), 6.83 (d, 1H, J=2.5 Hz), 6.85 (d, 1H, J=2.5 Hz), 7.20–7.33 (m, 4H, Ph).

Example 15

Preparation of 5,7-Bis[(1H-tetrazol-5-yl)methoxy]-3-(4-nitrobenzyl)-4-methyl-2H-1-benzopyran-2-one a) 5,7-Dihydroxy-4-methyl-3-(4-nitrobenzyl)-2H-1-benzopyran-2-one

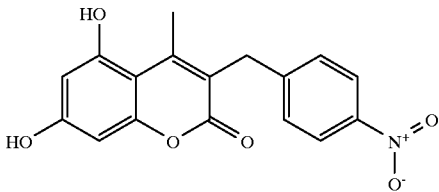

A solution of phloroglucinol (0.48 g) and ethyl 2-(4-nitrobenzyl)acetoacetate (1.00 g) in ethanol (150 ml) was treated with dry HCl at 0° C. for 7.5 hours and the solution was kept at that temperature overnight. Solvent was evaporated and the precipitate triturated with water. Yield 0.63 g (51%). Melting point 280–285° C.

$^1$H-NMR (DMSO-$d_6$, 300 MHz): 2.53 (s, 3H, CH$_3$), 4.03 (s, 2H, CH$_2$), 6.19 (d, 1H, J=2.4 Hz), 6.29 (d, 1H, J=2.4 Hz), 7.40–7.51 and 8.11–8.17 (m, 4H, Ph), 10.25 (s, 1H, OH), 10.52 (s, 1H, OH).

b) 5,7-Bis(cyanomethoxy)-3-(4-nitrobenzyl)-4-methyl-2H-1-benzopyran-2-one

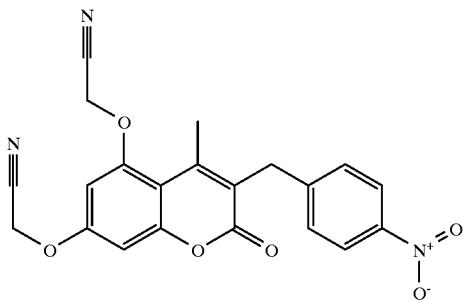

The product from the previous example (0.57 g), chloroacetonitrile (0.27 g) and potassium carbonate (1.20 g) were heated in DMF (2 ml) at 100° C. for 50 minutes. The product was isolated as described in example 1b. Yield 0.47 g (67%). Melting point 178–185° C.

$^1$H-NMR (DMSO-$d_6$, 400 MHz): 2.53 (s, 3H, CH$_3$), 4.11(s, 2H, CH$_2$), 5.319 (s, 2H, OCH$_2$CN), 5.323 (s, 2H, OCH$_2$CN), 6.83 (d, 1H, J=2.4 Hz), 6.96 (d, 1H, J=2.4 Hz), 7.48–7.53 and 8.12–8.16 (m, 4H, Ph).

c) 5,7-Bis[(1H-tetrazol-5-yl)methoxy]-3-(4-nitrobenzyl)-4-methyl-2H-1-benzopyran-2-one

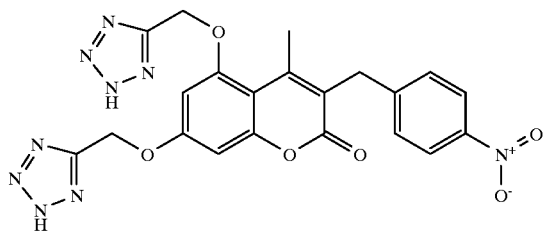

The product from the previous example (0.38 g), sodium azide (0.12 g) and ammonium chloride (0.11 g) were heated in DMF (3 ml) at 100° C. for 2 hours. The product was isolated as described in example 1c. Yield 0.25 g (54%). Melting point 240–244° C.

$^1$H-NMR (DMSO-$d_6$, 400 MHz): 2.47 (s, 3H, CH$_3$), 4.08 (s, 2H, CH$_2$), 5.611(s, 2H, OCH$_2$Tet), 5.623 (s, 2H, OCH$_2$Tet), 6.85 (d, 1H, J=2.4 Hz), 6.87 (d, 1H, J=2.4 Hz), 7.46–7.50 and 8.12–8.16 (m, 4H, Ph).

Example 16

Preparation of 5,7-Bis[(1H-tetrazol-5-yl)methoxy]-3-cyclopentyl-4-methyl-2H-1-benzopyran-2-one a) 3-Cyclopentyl-5,7-dihydroxy-4-methyl-2H-1-benzopyran-2-one

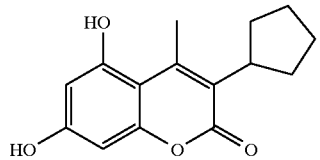

A solution of phloroglucinol (2.00 g) and ethyl 2-cyclopentylacetoacetate (3.14 g) in ethanol (40 ml) was treated with dry HCl at 0° C. for 2.5 hours and the solution kept at that temperature overnight. Solvent was evaporated and the precipitate purified with flash chromatography eluting with toluene-EtOAc-AcOH (8:1:1). Yield 1.22 g (29%).

$^1$H-NMR (DMSO-$d_6$, 300 MHz): 1.50–1.88 (m, 8H, —(CH$_2$)$_4$—), 2.57 (s, 3H, CH$_3$), 3.25 (m, 1H, CH), 6.11(d, 1H, J=2.4 Hz), 6.25 (d, 1H, J=2.4 Hz), 10.25 (b, 2H, OH).

b) 5,7-Bis(cyanomethoxy)-3-cyclopentyl-4-methyl-2H-1-benzopyran-2-one

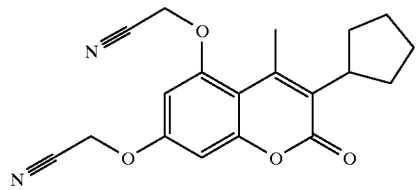

The product from the previous example (0.50 g), chloroacetonitrile (0.31 g) and potassium carbonate (0.61 g) were heated in DMF (2 ml) at 80° C. for 40 minutes. The product was isolated as described in example 1b. Yield 0.56 g (86%).

$^1$H-NMR (DMSO-$d_6$, 300 MHz): 1.55–1.90 (m, 8H, —(CH$_2$)$_4$—), 2.56 (s, 3H, CH$_3$), 3.37 (m, 1H, CH), 5.29 (s, 2H, OCH$_2$CN), 5.31(s, 2H, OCH$_2$CN), 6.75 (d, 1H, J=2.5 Hz), 6.88 (d, 1H, J=2.5 Hz).

c) 5,7-Bis[(1H-tetrazol-5-yl)methoxy]-3-cyclopentyl-4-methyl-2H-1-benzopyran-2-one

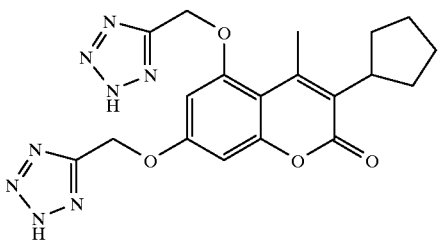

The product from the previous example (0.30 g), sodium azide (0.13 g) and ammonium chloride (0.11 g) were heated in DMF (1 ml) at 100° C. for 1.5 hours. The product was isolated as described in example 1c. Yield 0.30 g (80%). Melting point 248–252° C.

$^1$H-NMR (DMSO-$d_6$, 400 MHz): 1.53–1.89 (m, 8H, —(CH$_2$)$_4$—), 2.51(s, 3H, CH$_3$), 3.34 (m, 1H, CH), 5.59 (s, 2H, OCH$_2$Tet), 5.61(s, 2H, OCH$_2$Tet), 6.80 (s, 2H).

Example 17

Preparation of 5,7-Bis[(1H-tetrazol-5-yl)methoxy]-4-methyl-3-(1-naphtylmethyl)-2H-1-benzopyran-2-one a) 5,7-dihydroxy-4-methyl-3-(1-naphtylmethyl)-2H-1-benzopyran-2-one

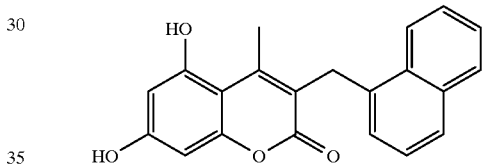

A solution of phloroglucinol (0.47 g) and ethyl 2-(1-naphtylmethyl)acetoacetate (1.00 g) in ethanol (20 ml) was treated with dry HCl at 0° C. for 3 hours and the solution kept at that temperature overnight. Solvent was evaporated and the precipitate triturated with water and recrystallized from isopropanol-water (1:1). Yield 0,96 g (78%). Melting point 275–280° C.

$^1$H-NMR (DMSO-$d_6$, 400 MHz): 2.45 (s, 3H, CH$_3$), 4.32 (s, 2H, CH$_2$), 6.23 (d, 1H, J=2.5 Hz), 6.32 (d, 1 H, J=2.5 Hz), 6.97–8.25 (m, 7H, Naph), 10.26 (s,1H, OH), 10.53 (s,1H, OH).

b) 5,7-Bis(cyanomethoxy)-4-methyl-3-(1-naphtylmethyl)-2H-1-benzopyran-2-one

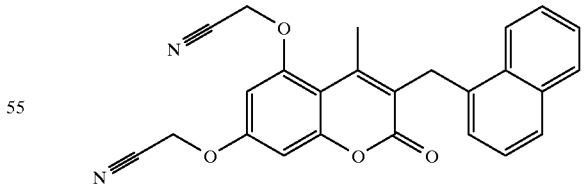

The product from the previous example (0.80 g), chloroacetonitrile (0.36 g) and potassium carbonate (0.66 g) were heated in DMF (4 ml) at 100° C. for 1 hour. The product was isolated as in example 1b. Yield 0.30 g (30%).

$^1$H-NMR (DMSO-$d_6$, 300 MHz): 2.45 (s, 3H, CH$_3$), 4.40 (s, 2H, CH$_2$), 5.34 (s, 2H, OCH$_2$CN), 5.36 (s, 2H, OCH$_2$CN), 6.86 (d, 1H, J=2.5 Hz), 7.010 (d, 1H, J=2.5 Hz), 7.016–8.27 (m, 7H, Naph).

c) 5,7-Bis[(1H-tetrazol-5-yl) methoxy]-4-methyl-3-(1-naphtylmethyl)-2H-1-benzopyran-2-one

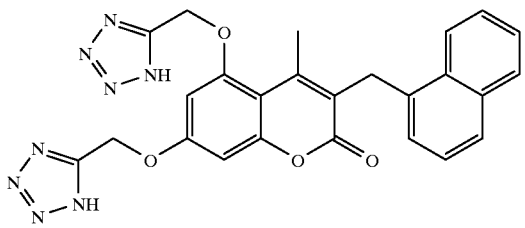

The product from the previous example (0.25 g), sodium azide (0.080 g) and ammonium chloride (0.072 g) were heated in DMF (2 ml) at 100° C. for 2.5 hours. The product was isolated as described in example 1c. Yield 0.11 g (36%). Melting point 164–174° C.

$^1$H-NMR (DMSO-$d_6$, 300 MHz): 2.40 (s, 3H, $CH_3$), 4.37 (s, 2H, $CH_2$), 5.63 (s, 2H, $OCH_2$Tet), 5.65 (s, 2H, $OCH_2$Tet), 6.87 (d, 1H, J=2.5 Hz), 6.92 (d, 1H, J=2.5 Hz), 6.98–8.26 (m, 7H, Naph).

Example 18

Preparation of 1-Benzyl-5,7-bis-[(1H-tetrazol-5-yl)-methoxy]-4-methyl-2(1H)quinolinone a) 5,7-Dimethoxy-4-methyl-2(1H)-quinolinone

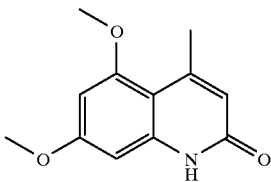

tert-Butyl acetoacetate (1.58 g) was heated to 120° C. and 3,5-dimethoxyaniline (1.53 g) dissolved in xylene (4 ml) was added. The mixture was heated at 120–130° C. for 20 minutes and then cooled to room temperature. Methanesulfonic acid (2 ml) was added and the mixture was stirred at ambient temperature for 10 minutes. Water (40 ml) was added and the precipitate filtered and dried. Yield 1.31 g (60%).

$^1$H-NMR (DMSO-$d_6$, 300 MHz): 2.50 (s, 3H, $CH_3$), 3.79 (s, 3H, $OCH_3$), 3.83 (s, 3H, $OCH_3$), 6.03 (s, 1H, CH=C), 6.31(d, 1H, J=2.3 Hz), 6.45 (d, 1H, J=2.3 Hz), 11.4 (b, 1H, NH).

b) 1-Benzyl-5,7-dimethoxy-4-methyl-2(1H)-quinolinone

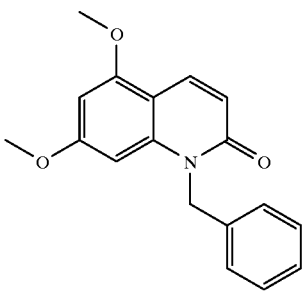

The product from the previous example (1.20 g) was suspended to DMSO (15 ml) and t-BuOK (0.68 g) and benzylbromide (1.03 g) were added. Reaction mixture was stirred at ambient temperature overnight. Water was added and the product extracted to EtOAc. EtOAc was dried and evaporated to dryness. The product was recrystallized from toluene. Yield 0.80 g (47%).

$^1$H-NMR (DMSO-$d_6$, 300 MHz): 2.55 (d, 3H, J=1.1 Hz, $CH_3$), 3.71 (s, 3H, $OCH_3$), 3.84 (s, 3H, $OCH_3$), 5.48 (b, 2H, $NCH_2$), 6.29 (d,1H, J=1.1 Hz, CH=C), 6.4 (s, 2H), 7.18–7.33 (m, 5H, Ph).

c) 1-Benzyl-5,7-dihydroxy-4-methyl-2(1H)-quinolinone

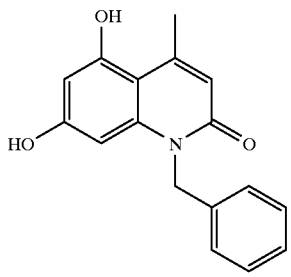

The product from the previous example (0.69 g) was dissolved to $CH_2Cl_2$ (14 ml) and the reaction mixture cooled to −20° C. $BBr_3$ (2.4 g) in $CH_2Cl_2$ (1 M solution) was added and the mixture was allowed to warm to ambient temperature during the night. The precipitate was filtered, washed with $CH_2Cl_2$ and dissolved to EtOAc. EtOAc was washed with dilute HCl, dryed and evapotated to dryness. Yield 0.34 g (54%).

$^1$H-NMR (DMSO-$d_6$, 300 MHz): 2.56 (d, 3H, J=1.0 Hz, $CH_3$), 5.33 (b, 2H, $NCH_2$), 6.11(d, 1H, J=2.1 Hz), 6.13 (d,1H, J=1.0 Hz, CH=C), 6.17 (d, 1H, J=2.1 Hz), 7.12–7.34 (m, 5H, Ph), 9.90 (b, 1H, OH), 10.22 (s, 1H, OH).

d) 1-Benzyl-5,7-bis(cyanomethoxy)-4-methyl-2(1H)-quinolinone

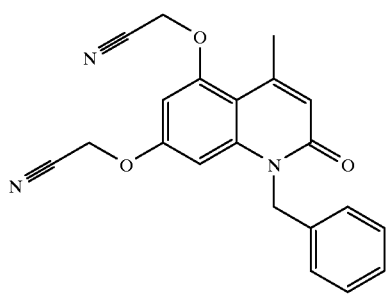

The product from the previous example (0.34 g), chloroacetonitrile (0.13 g) and potassium carbonate (0.34 g) were heated in DMF (2 ml) at 100° C. for 1.5 hours. Water was added and the precipitate filtered and dried. The product was recrystallized from isopropanol. Yield 0.20 g (46%).

$^1$H-NMR (DMSO-$d_6$, 400 MHz): 2.57 (s, 3H, $CH_3$), 5.22 (s, 2H, $OCH_2CN$), 5.30 (s, 2H, $OCH_2CN$), 5.50 (b, 2H, $NCH_2$), 6.42 (s, 1H, CH=C), 6.70 (d, 1H, J=2.1 Hz), 6.73 (d, 1H, J=2.1 Hz), 7.21–7.32 (m, 5H, Ph).

e) 1-Benzyl-5,7-bis-[(1H-tetrazol-5-yl)methoxy]-4-methyl-2(1H)-quinolinone

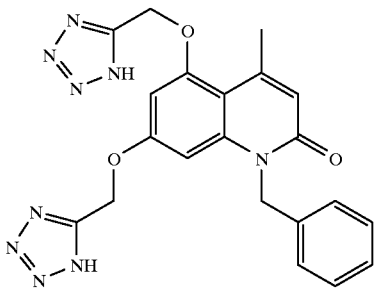

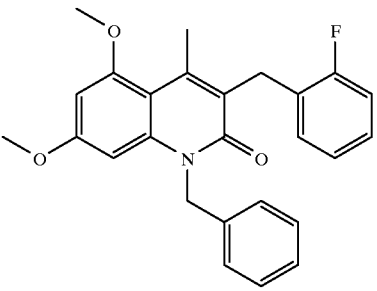

The product from the previous example (0.20 g), sodium azide (0.072 g) and ammonium chloride (0.060 g) were heated in DMF (2 ml) at 100° C. for 3 hours. The product was isolated as described in example 1c. Yield 0.21 g (85%). Melting point 246–249° C.

$^1$H-NMR (DMSO-d$_6$, 400 MHz): 2.50 (s, 3H, CH$_3$), 5.48 (b, 4H, OCH$_2$Tet, NCH$_2$), 5.60 (s, 2H, OCH$_2$Tet), 6.34 (s, 1H, CH=C), 6.64 (d, 1H, J=1.9 Hz), 6.77 (d, 1H, J=1.9 Hz), 7.18–7.32 (m, 5H, Ph).

Example 19

Preparation of 1-Benzyl-5,7-bis[1H-tetrazol-5-yl)methoxy]-3-(2-fluorobenzyl)-4-methyl-2(1H)-quinolinone a) 5,7-Dimethoxy-3-(2-fluorobenzyl)-4-methyl-2(1H)-quinolinone

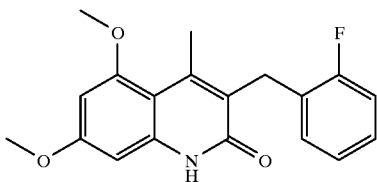

Ethyl 2-(2-fluorobenzyl)acetoacetate (2.5 g) in xylene (1 ml) was heated to 150° C. and 3,5-dimethoxyaniline (1.46 g) in xylene (4 ml) was added in small portions during 30 minutes. The reaction mixture was heated at 160° C. for 3 hours and then cooled to room temperature. Methanesulfonic acid (1.7 ml) was added and the mixture was stirred at ambient temperature for 30 minutes. Water was added and the precipitate filtered and dried. The product was triturated with warm ethanol. Yield 0.64 g (21%).

$^1$H-NMR (DMSO-d$_6$, 300 MHz): 2.45 (s, 3H), 3.79 (s, 3H), 3.82 (s, 3H), 3.97 (s, 2H), 6.33 (d, 1H, J=2.4 Hz), 6.48 (d, 1H, J=2.4 Hz), 6.90–7.25 (m, 4H), 11.61(s, 1H).

b) 1-Benzyl-5,7-dimethoxy-3-(2-fluorobenzyl)-4-methyl-2(1H)-quinolinone

The product from the previous example (0.62 g) was treated with t-BuOK (0.23 g) and benzylbromide (0.36 g) in DMSO (12 ml) at 60° C. for 2.5 hours. The product was isolated as described in example 18b. Yield 0.39 g (49%).

$^1$H-NMR (DMSO-d$_6$, 400 MHz): 2.51(s, 3H), 3.72 (s, 3H), 3.84 (s, 3H), 4.11(s, 2H), 5.55 (b, 2H), 6.433 (d, 1H, J=2.1 Hz), 6.443 (d, 1H, J=2.1 Hz), 6.97–7.33 (m, 9H).

c) 1-Benzyl-5,7-dihydroxy-3-(2-fluorobenzyl)-4-methyl-2(1H)-quinolinone

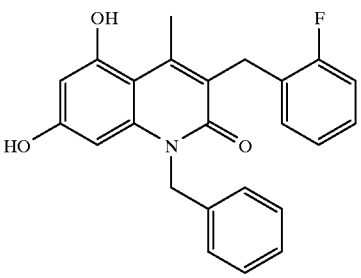

The product from the previous example (0.34 g) was treated with BBr$_3$ (8.48 g) in CH$_2$Cl$_2$ (7 ml) as described in example 18c. Yield 0.30 g (82%).

$^1$H-NMR (DMSO-d$_6$, 400 MHz): 2.55 (s, 3H), 4.06 (s, 2H), 5.40 (b, 2H), 6.13 (d, 1H, J=2.1 Hz), 6.22 (d, 1H, J=2.1 Hz), 6.97–7.33 (m, 9H), 10.3 (b, 2H).

d) 1-Benzyl-5,7-bis(cyanomethoxy)-3-(2-fluorobenzyl)-4-methyl-2(1H)-quinolinone

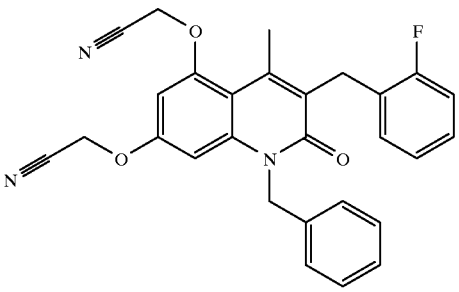

The product from the previous example (0.21 g), chloroacetonitrile (0.086 g) and potassium carbonate (0.37 g) were heated in DMF (2 ml) at 100° C. for 2 hours. The product was isolated as described in example 1b. Yield 0.18 g (71%).

$^1$H-NMR (DMSO-d$_6$, 400 MHz): 2.53 (s, 3H), 4.13 (s, 2H), 5.23 (s, 2H), 5.29 (s, 2H), 5.57 (b, 2H), 6.746 (d, 1H, J=2.3 Hz), 6.756 (d, 1H, J=2.3 Hz), 7.00–7.32 (m, 9H).

e) 1-Benzyl-5,7-bis[1H-tetrazol-5-yl)methoxy]-3-(2-fluorobenzyl)-4-methyl-2(1H)-quinolinone

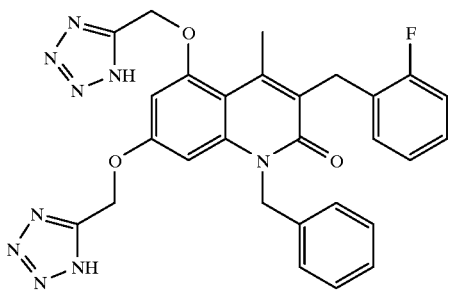

The product from the previous example (0.17 g), sodium azide (0.051 g) and ammonium chloride (0.042 g) were heated in DMF at 100° C. for 3 hours. The product was isolated as described in example 1c. Yield 0.17 g (85%). Melting point 135–140° C.

$^{1}$H-NMR (DMSO-d$_{6}$, 400 MHz): 2.46 (s, 3H), 4.10 (s, 2H), 5.48 (s, 2H), 5.51(b, 2H), 5.59 (s, 2H), 6.68 (d, 1H, J=2.2 Hz), 6.79 (d, 1H, J=2.2 Hz), 6.99–7.32 (m, 9H).

Example 20

Preparation of 1-Benzyl-5,7-bis[1H-tetrazol-5-yl)-methoxy]-4-methyl-3-(2-phenylethyl)-2(1H)-quinolinone a) 5,7-Dimethoxy-4-methyl-3-(2-phenylethyl)-2(1H)-quinolinone

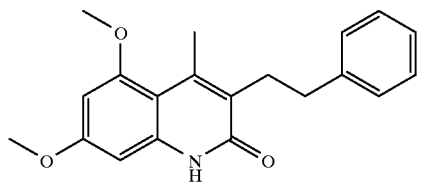

Ethyl 2-(2-phenylethyl)acetoacetate (2.70 g) in xylene (5 ml) was treated with 3,5-dimethoxyaniline (1.60 g) at 150° C. as described in example 19a. Methanesulfonic acid (4.0 ml) was added at room temperature and the mixture heated at 80° C. for 1 hour. The product was isolated as described in example 19a. Yield 1.38 g (41%).

$^{1}$H-NMR (DMSO-d$_{6}$, 400 MHz): 2.45 (s, 3H), 2.64–2.68 (m, 2H), 2.82–2.86 (m, 2H), 3.78 (s, 3H), 3.81(s, 3H), 6.30 (d, 1H, J=2.3 Hz), 6.45 (d, 1H, J=2.3 Hz), 7.18–7.30 (m, 5H), 11.45 (s,1H).

b) 1-Benzyl-5,7-dimethoxy-4-methyl-3-(2-phenylethyl)-2(1H)-quinolinone

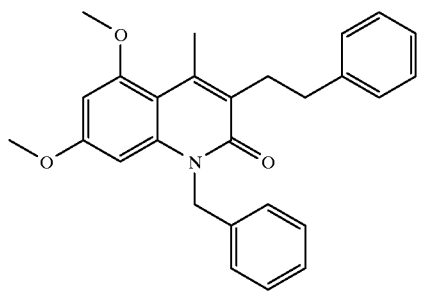

The product from the previous example (0.61 g), t-BuOK (0.24 g) and benzylbromide (0.36 g) were heated in DMSO (12 ml) at 60° C. for 2 hours. The product was isolated as described in example 18b. Yield 0.31 g (40%).

$^{1}$H-NMR (DMSO-d$_{6}$, 400 MHz): 2.51(s, 3H), 2.73–2.77 (m, 2H), 2.96–3.00 (m, 2H), 3.70 (s, 3H), 3.83 (s, 3H), 5.55 (b, 2H), 6.40 (s, 2H), 7.17–7.33 (m, 10H).

c) 1-Benzyl-5,7-dihydroxy-4-methyl-3-(2-phenylethyl)-2(1H)-quinolinone

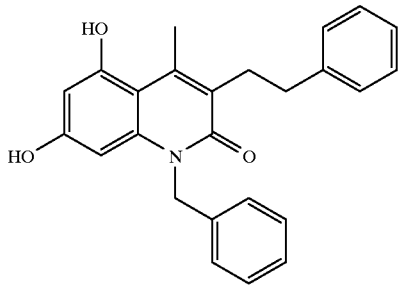

The product from the previous example (0.31 g) was treated with BBr$_{3}$ (0.75 g) in CH$_{2}$Cl$_{2}$ (5 ml) as in example 18c. Yield 0.26 g (89%).

$^{1}$H-NMR (DMSO-d$_{6}$, 300 MHz): 2.56 (s, 3H), 2.69–2.75 (m, 2H), 2.90–2.95 (m, 2H), 5.39 (b, 2H), 6.08 (d, 1H, J=2.0 Hz), 6.19 (d, 1H, J=2.0 Hz), 7.11–7.33 (m, 10H), 10.2 (b, 2H).

d) 1-Benzyl-5,7-bis(cyanomethoxy)-4-methyl-3-(2-phenylethyl)-2(1H)-quinolinone

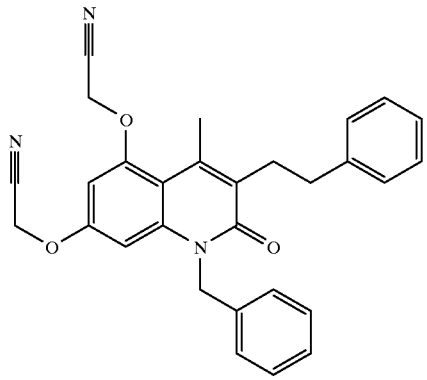

The product from the previous example (0.22 g), chloroacetonitrile (0.091g) and potassium carbonate (0.39 g) were heated at 100° C. for 2 hours. The product was isolated as in example 1b. Yield 0.20 g (76%).

$^{1}$H-NMR (DMSO-d$_{6}$, 400 MHz): 2.50 (s, 3H), 2.73–2.77 (m, 2H), 2.98–3.02 (m, 2H), 5.21(s, 2H), 5.29 (s, 2H), 5.56 (b, 2H), 6.70 (d, 1H, J=2.1 Hz), 6.72 (d, 1H, J=2.1 Hz), 7.18–7.33 (m, 10H).

e) 1-Benzyl-5,7-bis[1H-tetrazol-5-yl)methoxy]-4-methyl-3-(2-phenylethyl)-2(1H)-quinolinone

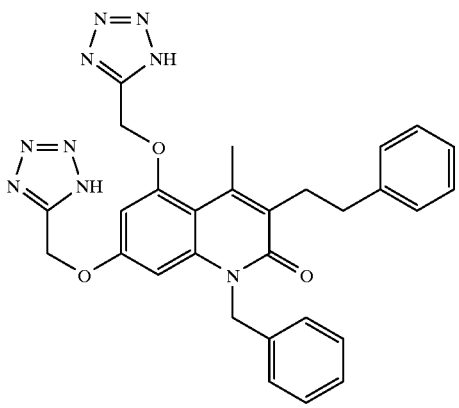

The product from the previous example (0.19 g), sodium azide (0.057 g) and ammonium chloride (0.047 g) were heated in DMF at 100° C. for 3 hours. The product was isolated as described in example 1c. Yield 0.18 g (78%). Melting point 215–218° C.

$^1$H-NMR (DMSO-$d_6$, 400 MHz): 2.46 (s, 3H), 2.70–2.74 (m, 2H), 2.95–2.99 (m, 2H), 5.47 (s, 2H), 5.54 (b, 2H), 5.57 (s, 2H), 6.64 (d, 1H, J=2.0 Hz), 6.77 (d, 1H, J=2.0 Hz), 7.16–7.33 (m, 10H).

Example 21

Preparation of 5,7-Bis(aminocarbonylmethoxy)-1,3-dibenzyl-4-methyl-2(1H)-quinolinone

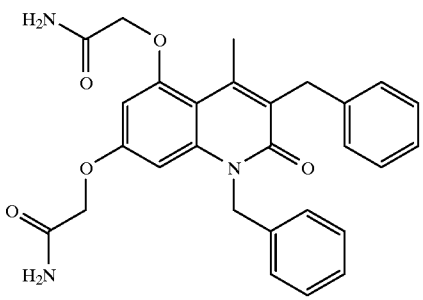

The mixture of 5,7-dihydroxy-1,3-dibenzyl-4-methyl-2 (1H)-quinolinone (0.5 g), potassium carbonate (0.9 g) and 2-chloroacetamide ( 0.25 g) in DMF (6.5 ml) were reacted at 100° C. for two hours. The reaction mixture was treated with ice water and filtered. The product was triturated with hot ethanol. Yield: 0.32 g. Melting point 252–253° C.

$^1$H-NMR (400 MHz, DMSO-$d_6$): 2.63 (s, 3H, CH3), 4.13 (s, 2H, PhCH$_2$), 4.37 (s, 2H, OCH$_2$), 4.55 (s, 2H, OCH$_2$), 5.54 (s, 2H, NCH$_2$Ph), 6.40 (d, 1H, J=2 Hz, ArH), 6.53 (d, 1H, J=2 Hz, ArH), 7.13–7.33 (m, 10 H, Ph), 7.44 (d, 2H, J=65 Hz, CONH$_2$), 7.47 (d, 2H, J=68 Hz, CONH$_2$).

Example 22

Preparation of 5,7-Bis(ethoxycarbonylmethoxy)-1,3-dibenzyl-4-methyl-2(1H)-quinolinone

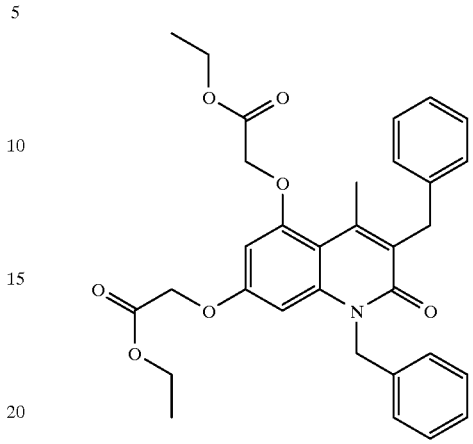

The mixture of 5,7-dihydroxy-1,3-dibenzyl-4-methyl-2 (1H)-quinolinone (1 g), ethyl 2-bromoacetate (0.63 ml) and potassium carbonate (1.49 g) in DMF (5 ml) was heated under nitrogen at 110° C. for three hours, poured into ice water and filtered. The resulting solid material was triturated with ether and filtered again. Yield: 1.03 g, melting point 113–116° C.

$^1$H-NMR (400 MHz, DMSO-$d_6$): 1.15 (t, 3H, CH$_3$CH$_2$, J=7.1 Hz), 1.20 (t, 3H, CH$_3$CH$_2$, J=7.1 Hz), 2.63 (s, 3H, CH3), 4.03 (q, 2H, CH$_2$CH$_3$, J=7.1 Hz), 4.13 (s, 2H, CH$_2$Ph), 4.17 (q, 2H, CH$_2$CH$_3$, J=7.1 Hz), 4.78 (s, 2H, OCH$_2$), 4.90 (s, 2H, OCH$_2$), 6.41(d, 1H, J=2.2 Hz), 6.44 (d, 1H, J=2.2 Hz), 7.13–7.33 (m, 10 H, Ph).

Example 23

Preparation of 5,7-Bis (hydroxyaminocarbonylmethoxy)-1,3-dibenzyl-4-methyl-2(1H)-quinolinone

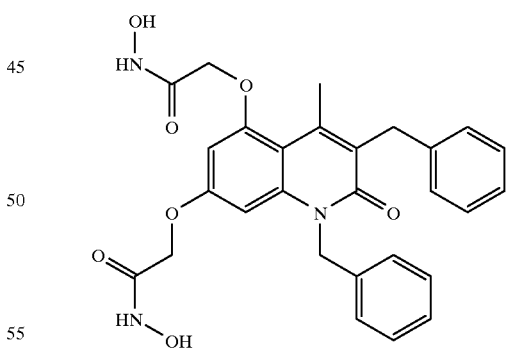

The product from the previous example (0.3 g), hydroxylamine hydrochloride (0.32 g) and 5 N NaOH (1.05 ml) were reacted in ethanol (8 ml) at 50° C. for six hours. The reaction mixture was treated with water and made basic (pH 10) and filtered. The filtrate was acidified to pH 2 and filtered. Yield: 0.2 g, melting point 121–127° C.

$^1$H-NMR (400 MHz, DMSO-$d_6$): the tautomeric forms of hydroxamic acid are seen in OCH$_2$-signals: 2.63 (s,3H, CH3), 4.13 (S, 2H, CH$_2$Ph), 4.41(s, 2H, OCH$_2$), 4.54 (s, 2H,OCH$_2$), 4.64 (s, 2H, HON=C(OH)CH$_2$O), 4.65 (s, 2H, HON=C(OH)CH₂O), 4.77 (s, 2H, HON=C(OH)CH₂O), 4.78 ( (s, 2H, HON=C(OH)CH₂O), 5.54 (s, 2H, NCH₂Ph), 6.38–6.54 (m, 2H, ArH), 7.14–7.34 (m, 10 H, Ph), 9.05 (b, 2H, NOH), 10.84 (s,1H, HONHCO), 10.88 (s, 1H, HONHCO).

Example 24

Preparation of 5,7-Bis -[1-(6-hydroxypyridazinyl)] oxy-1,3-dibenzyl-4-methyl-2(1H)-quinolinone a) 5,7-Bis -[1-(6-chloropyridazinyl)]oxy-1,3-dibenzyl-4-methyl-2(1H)-quinolinone

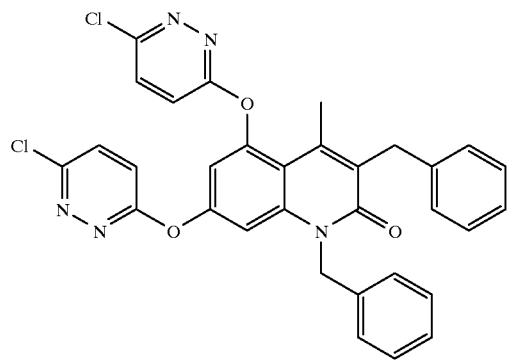

A mixture of 1,3-dibenzyl-5,7-dihydroxy-4-methyl-2 (1H)-quinolinone (0.5 g), 3,6-dichloropyridazine (0.83 g) and potassium carbonate (0.75 g) in DMF (12,5 ml) was stirred at 80° C. for 4 hours. The reaction mixture was treated with water at pH 8 and filtered. The solids were recrystallized from ethanol-DMF (2:1). Yield 0.5 g. Melting point 208–218° C.

¹H-NMR (DMSO-d6, 300 MHz): 2.43 (s, 3H, CH₃), 4.16 (s, 2H, CH₂Ph), 5.58 (s, 2H, NCH₂Ph), 7.09–7.33 (m, 12H, ArH+Ph), 7.55 (d,1H, PyridH, J=9,2 Hz), 7.70 (d, 1H, PyridH, J=9,2 Hz),7.93 (d, 1H, PyridH, J=9,2 Hz), 7.98 (d, 1H, PyridH, J=9,2 Hz).

b) 5,7-Bis-[1-(6-hydroxypyridazinyl)]oxy-1,3-dibenzyl-4-methyl-2(1H)-quinolinone

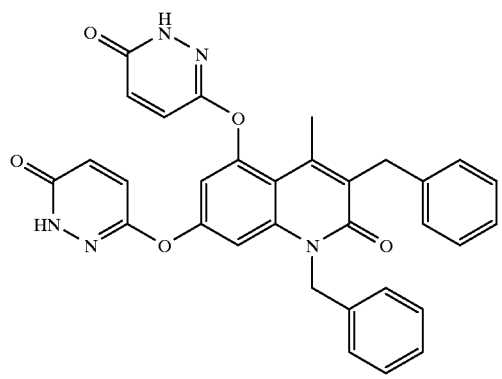

The product from the previous example (0.2 g) and potassium acetate (0.13 g) in acetic acid (5 ml) were refluxed for 4 hours. The mixture was evaporated, treated with water at pH 10 and filtered. The filtrate was acidified to pH 6 and filtered. Yield 70 mg.

¹H-NMR (DMSO-d6, 300 MHz): 2.47 (s, 3H, CH₃), 4.15 (s, 2H, CH₂Ph), 5.55 (s, 2H, NCH₂), 6.93–7.34 (m, 15H, PyridH+ArH+Ph), 7.47 (d, 1H, J=10 Hz), 12.25 (s, 1H, NH), 12.38 (s, 1H NH).

We claim:

1. A method of treating or preventing stunned myocardium, comprising:

administering a therapeutically effective amount of a phospholamban inhibitor to a mammal in need of such treating or preventing.

2. The method of claim 1, wherein said stunned myocardium occurs in association with ischemia-reperfusion.

3. The method of claim 1, wherein said stunned myocardium occurs in association with a pathological condition selected from the group consisting of unstable angina and valvular heart disease.

4. The method of claim 1, wherein said stunned myocardium occurs in association with a cardiovascular intervention procedure selected from the group consisting of thrombolysis of myocardial infarction, coronary balloon angioplasty, coronary stent implantation, coronary artery bypass surgery, coronary atherectomy, heart transplantation and resuscitation.

5. The method of claim 4, wherein said cardiovascular intervention procedure is thrombolysis of myocardial infarction.

6. The method of claim 4, wherein said cardiovascular intervention procedure is coronary balloon angioplasty.

7. The method of claim 4, wherein said cardiovascular intervention procedure is coronary stent implantation.

8. The method of claim 4, wherein said cardiovascular intervention procedure is coronary artery bypass surgery.

9. The method of claim 4, wherein said cardiovascular intervention procedure is coronary atherectomy.

10. The method of claim 4, wherein said cardiovascular intervention procedure is heart transplantation.

11. The method of claim 4, wherein said cardiovascular intervention procedure is resuscitation.

12. The method of claim 1, wherein said phospholamban inhibitor is administered in a dosage of from about 0.1 to 500 mg per day.

13. The method of claim 12, wherein said phospholamban inhibitor is administered in a dosage of from about 0.5 to 50 mg per day.

14. A myocardial treatment procedure, comprising:

administering a phospholamban inhibitor in an amount effective to treat or prevent stunned myocardium to a mammal in need of such treating or preventing; and performing a cardiovascular intervention procedure selected from the group consisting of thrombolysis of myocardial infarction, coronary balloon angioplasty, coronary stent implantation, coronary artery bypass surgery, coronary atherectomy, heart transplantation and resuscitation.

15. The method of claim 14, wherein said cardiovascular intervention procedure is thrombolysis of myocardial infarction.

16. The method of claim 14, wherein said cardiovascular intervention procedure is coronary balloon angioplasty.

17. The method of claim 14, wherein said cardiovascular intervention procedure is coronary stent implantation.

18. The method of claim 14, wherein said cardiovascular intervention procedure is coronary artery bypass surgery.

19. The method of claim 14, wherein said cardiovascular intervention procedure is coronary atherectomy.

20. The method of claim 14, wherein said cardiovascular intervention procedure is heart transplantation.

21. The method of claim 14, wherein said cardiovascular intervention procedure is resuscitation.

22. The method of claim 14, wherein said phospholamban inhibitor is administered in a dosage of from about 0.1 to 500 mg per day.

23. The method of claim 22, wherein said phospholamban inhibitor is administered in a dosage of from about 0.5 to 50 mg per day.

* * * * *